(12) United States Patent
Boyle et al.

(10) Patent No.: US 7,423,023 B2
(45) Date of Patent: Sep. 9, 2008

(54) ENHANCEMENT OF IMMUNE RESPONSE USING TARGETING MOLECULES

(75) Inventors: Jeffrey Stephen Boyle, Heidelberg (AU); Jamie Louise Brady, Brunswick (AU); Andrew Mark Lew, Essendon (AU)

(73) Assignee: CSL, Limited, Victoria (AU)

( * ) Notice: Subject to any disclaimer, the term of this patent is extended or adjusted under 35 U.S.C. 154(b) by 456 days.

(21) Appl. No.: 10/185,799

(22) Filed: Jun. 28, 2002

(65) Prior Publication Data

US 2003/0072742 A1    Apr. 17, 2003

Related U.S. Application Data

(63) Continuation of application No. 09/402,020, filed as application No. PCT/AU98/00208 on Mar. 26, 1998, now abandoned.

(30) Foreign Application Priority Data

Mar. 27, 1997  (AU) .................... PO5891
Feb. 13, 1998  (AU) .................... PP1830

(51) Int. Cl.
*A61K 31/713*    (2006.01)

(52) U.S. Cl. .................................... 514/44

(58) Field of Classification Search ............ None
See application file for complete search history.

(56) References Cited

U.S. PATENT DOCUMENTS

| | | | |
|---|---|---|---|
| 5,434,131 A * | 7/1995 | Linsley et al. ............ | 514/2 |
| 5,698,679 A | 12/1997 | Nemazee ................ | 530/387.3 |
| 5,851,795 A | 12/1998 | Linsley et al. ............ | 435/69.1 |
| 6,080,409 A | 6/2000 | Laus et al. ............... | 424/192.1 |
| 6,224,870 B1 | 5/2001 | Segal ...................... | 424/192.1 |
| 6,719,972 B1 * | 4/2004 | Gribben et al. .......... | 424/154.1 |

FOREIGN PATENT DOCUMENTS

WO    WO 96/40941    12/1996

OTHER PUBLICATIONS

Hodgson et al., Infection and Immunity, 1994, 62: 5275-5280.*

Baier et al., "Immunogenic targeting of recombinant peptide vaccines to human antigen-presenting cells by chimeric anti-HLA-DR and anti-surface immunoglobulin D antibody fab fragments in vitro," *J. Virol.*, 69(4):2357-2365, 1995.

Boyle et al., "Enhanced responses to a DNA vaccine encoding a fusion antigen that is directed to sites of immune induction," *Nature*, 392:408-411, 1998.

Brumeanu et al., "Engineering of doubly antigenized immunoglobulins expressing T and B viral epitopes," *Immunotechnology*, 2:85-95, 1996.

Corthesy et al., "A pathogen-specific epitope inserted into recombinant secretory immunoglobulin A is immunogenic by the oral route," *J. Biol. Chem.*, 271(52):33670-33677, 1996.

Huang et al., "Enhanced antitumor immunity by fusion of CTLA-4 to a self tumor antigen," *Blood*, 96:3663-3669, 2000.

Lebens and Holmgren, "Mucosal vaccines based on the use of cholera toxin B subunit as immunogen and antigen carrier," *Dev. Biol. Stand.*, 82:215-217, 1994.

Liu et al., "FcγRI-targeted fusion proteins result in efficient presentation by human monocytes of antigenic and antagonistic T cell epitopes," *J. Clin. Invest.*, 98:2001-2007, 1996.

Skea et al., "Studies of the adjuvant-independent antibody response to immunotargeting. Target structure dependence, isotype distribution, and induction of long term memory," *J. Immunol.*, 151:3557-3568, 1993.

"CTLA-4-Ig" Mar. 25, 2006; hublog.hubmed.org/archives/001341.html, downloaded Oct. 15, 2007.

ORENCIA®, Mar. 2007, Bristol-Myers Squibb Company, Princeton, NJ 08543, USA.

Treating Systemic Lupus Erythematosus (SLE) Patients with CTLA4-IgG4m (RG2077), clinicaltrials.gov/ct/show/NCT0094380?order=1, downloaded Oct. 4, 2007.

So et al., Immunitherapeutic Effects of CTLA4Ig Fusion Protein on Murine EAE and GVHD, *Immune Netw.*, Dec. 2003, vol. 3, No. 4, pp. 302-309, Abstract only, koreamed.org/DisplaySearchResultText.php, downloaded Oct. 4, 2007.

Shiraishi et al., "Prevention of Acute Lung Allograft Rejection in Rat by CTLA4Ig," *American Journal of Transplantation*, 2002, vol. 2, pp. 223-228, Blackwell Munksgaard, 2002.

* cited by examiner

*Primary Examiner*—Ilia Ouspenski
(74) *Attorney, Agent, or Firm*—Foley & Lardner LLP

(57) ABSTRACT

The present invention provides methods of enhancing the immune response to an immunogen and to compositions for use in these methods. In particular the present invention provides a DNA molecule for use in raising an immune response to an antigen. The DNA molecule includes a first sequence encoding a targeting molecule, a second sequence encoding the antigen or an epitope thereof, and optionally a third sequence encoding a polypeptide which promotes dimerization or multimerization of the product encoded by the DNA molecule.

7 Claims, 20 Drawing Sheets

SEQUENCE LISTING

<160> NUMBER OF SEQ ID NOS: 1

<210> SEQ ID NO 1
<211> LENGTH: 11265
<212> TYPE: DNA
<213> ORGANISM: Murine

<400> SEQUENCE: 1

```
tctagagtcg accaattctc atgtttgaca gcttatcatc gcagatcctg agcttgtatg      60
gtgcactctc agtacaatct gctctgctgc cgcatagtta agccagtatc tgctccctgc     120
ttgtgtgttg gaggtcgctg agtagtgcgc gagcaaaatt taagctacaa caaggcaagg     180
cttgaccgac aattgcatga agaatctgct tagggttagg cgttttgcgc tgcttcgcga     240
tgtacgggcc agatatacgc gtatctgagg ggactagggt gtgtttaggc gcccagcggg     300
gcttcggttg tacgcggtta ggagtcccct caggatatag tagtttcgct tttgcatagg     360
gaggggaaa tgtagtctta tgcaatacac ttgtagtctt gcaacatggt aacgatgagt     420
tagcaacatg ccttacaagg agagaaaaag caccgtgcat gccgattggt ggaagtaagg     480
tggtacgatc gtgccttatt aggaaggcaa cagacaggtc tgacatggat tggacgaacc     540
actgaattcc gcattgcaga gataattgta tttaagtgcc tagctcgata caataaacgc     600
catttgacca ttcaccacat tggtgtgcac ctccaagctg ggtaccagct gctagcaagc     660
ttgctagcgg ccgctcgagc tcagcacatt tgccccccag ccatggcttg tcttggactc     720
cggaggtaca aagctcaact gcagctgcct tctaggactt ggccttttgt agccctgctc     780
actcttcttt tcatcccagt cttctctgaa gccatacagg tgacccaacc ttcagtggtg     840
ttggctagca gccatggtgt cgccagcttt ccatgtgaat attcaccatc acacaacact     900
gatgaggtcc gggtgactgt gctgcggcag acaaatgacc aaatgactga ggtctgtgcc     960
acgacattca cagagaagaa tacagtgggc ttcctagatt accccttctg cagtggtacc    1020
tttaatgaaa gcagagtgaa cctcaccatc caaggactga gagctgttga cacgggactg    1080
tacctctgca aggtggaact catgtaccca ccgccatact ttgtgggcat gggcaacggg    1140
acgcagattt atgtcattga tccagaacca tgcccggatt ctggtaagta taagcttcag    1200
cgctcctgcc tggacgcatc ccggctatgc agccccagtc cagggcagca aggcaggcc    1260
cgtctgcctc ttcacccgga gcctctgccc gccccactca tgctcaggga gagggtcttc    1320
tggcttttc ccaggctctg gcaggcaca ggctaggtgc ccctaaccca ggccctgcac    1380
acaaagggc aggtgctggg ctcagacctg ccaagagcca tatccgggag gaccctgccc    1440
ctgacctaag cccaccccaa aggccaaact ctccactccc tcagctcgga cacctctct    1500
cctcccagat tccagtaact cccaatcttc tctctgcaga gcccaaatct tgtgacaaaa    1560
ctcacacatg cccaccgtgc ccaggtaagc cagcccagc ctcgccctcc agctcaaggc    1620
gggacaggtg ccctagagta gcctgcatcc agggacaggc cccagccggg tgctgacacg    1680
tccacctcca tctcttcctc agcacctgaa ctcctggggg gaccgtcagt cttcctcttc    1740
ccccccaaaac ccaaggacac cctcatgatc tcccggaccc ctgaggtcac atgcgtggtg    1800
gtggacgtga gccacgaaga ccctgaggtc aagttcaact ggtacgtgga cggcgtggag    1860
gtgcataatg ccaagacaaa gccgcgggag gagcagtaca acagcacgta ccgggtggtc    1920
agcgtcctca ccgtcctgca ccaggactgg ctgaatggca aggagtacaa gtgcaaggtc    1980
tccaacaaag ccctcccagc ccccatcgag aaaaccatct ccaaagccaa aggtgggacc    2040
```

```
cgtggggtgc gagggccaca tggacagagg ccggctcggc ccaccctctg ccctgagagt    2100
gaccgctgta ccaacctctg tcctacaggg cagccccgag aaccacaggt gtacaccctg    2160
cccccatccc gggatgagct gaccaagaac caggtcagcc tgacctgcct ggtcaaaggc    2220
ttctatccca gcgacatcgc cgtggagtgg gagagcaatg ggcagccgga gaacaactac    2280
aagaccacgc ctcccgtgct ggactccgac ggctccttct tcctctacag caagctcacc    2340
gtggacaaga gcaggtggca gcaggggaac gtcttctcat gctccgtgat gcatgaggct    2400
ctgcacaacc actacacgca gaagagcctc tccctgtctc cgggtaaatg agtgcgacgg    2460
ccggatccag acatgataag atacattgat gagtttggac aaaccacaac tagaatgcag    2520
tgaaaaaaat gctttatttg tgaaatttgt gatgctattg ctttatttgt aaccattata    2580
agctgcaata aacaagttaa caacaacaat tgcattcatt ttatgtttca ggttcagggg    2640
gaggtgggga ggttttttaa agcaagtaaa acctctacaa atgtggtatg gctgattatg    2700
atccggctgc ctcgcgcgtt tcggtgatga cggtgaaaac ctctgacaca tgcagctccc    2760
ggagacggtc acagcttgtc tgtaagcgga tgccgggagc agacaagccc gtcaggcgc    2820 gtcagcgggt gttggcgggt gtcggggcgc agccatgacc ggtcgaccac tgggcgccag    2880
aaatccgcgc ggtggttttt gggggtcggg ggtgtttggc agccacagac gcccggtgtt    2940
cgtgtcgcgc cagtacatgc ggtccatgcc caggccatcc aaaaaccatg ggtctgtctg    3000
ctcagtccag tcgtggacca gaccccacgc aacgcccaaa ataataaccc ccacgaacca    3060
taaaccattc cccatggggg accccgtccc taacccacgg ggccagtggc tatggcaggg    3120
cctgccgccc cgacgttggc tgcgagccct gggccttcac ccgaacttgg ggggtggggt    3180
ggggaaaagg aagaaacgcg ggcgtattgg ccccaatggg gtctcggtgg ggtatcgaca    3240
gagtgccagc cctgggaccg aaccccgcgt ttatgaacaa cgacccaac acccgtgcgt    3300 tttattctgt cttttttattg ccgtcatagc gcgggttcct tccggtattg tctccttccg    3360
tgtttcagtt agcctccccc atctccccta ttcctttgcc ctcggacgag tgctggggcg    3420
tcggtttcca ctatcggcga gtacttctac acagccatcg gtccagacgg ccgcgcttct    3480
gcgggcgatt tgtgtacgcc cgacagtccc ggctccggat cggacgattg cgtcgcatcg    3540
accctgcgcc caagctgcat catcgaaatt gccgtcaacc aagctctgat agagttggtc    3600
aagaccaatg cggagcatat acgcccggag ccgcggcgat cctgcaagct ccggatgcct    3660
ccgctcgaag tagcgcgtct gctgctccat acaagccaac cacggcctcc agaagaagat    3720
gttggcgacc tcgtattggg aatccccgaa catcgcctcg ctccagtcaa tgaccgctgt    3780
tatgcggcca ttgtccgtca ggacattgtt ggagccgaaa tccgcgtgca cgaggtgccg    3840
gacttcgggg cagtcctcgg cccaaagcat cagctcatcg agagcctgcg cgacggacgc    3900
actgacggtg tcgtccatca cagtttgcca gtgatacaca tggggatcag caatcgcgca    3960
tatgaaatca cgccatgtag tgtattgacc gattccttgc ggtccgaatg ggccgaaccc    4020
gctcgtctgg ctaagatcgg ccgcagcgat cgcatccatg gcctccgcga ccggctgcag    4080
aacagcgggc agttcggttt caggcaggtc ttgcaacgtg acaccctgtg cacggcggga    4140
gatgcaatag gtcaggctct cgctgaattc cccaatgtca agcacttccg gaatcgggag    4200
cgcggccgat gcaaagtgcc gataaacata acgatctttg tagaaaccat cggcgcagct    4260
atttacccgc aggacatatc cacgccctcc tacatcgaag ctgaaagcac gagattcttc    4320
gccctccgag agctgcatca ggtcggagac gctgtcgaac ttttcgatca gaaacttctc    4380
```

-continued

```
gacagacgtc gcggtgagtt caggcttttt catatctcat tgcccgggat ctgcggcacg    4440
ctgttgacgc tgttaagcgg gtcgctgcag ggtcgctcgg tgttcgaggc cacacgcgtc    4500
accttaatat gcgaagtgga cctgggaccg cgccgcccg actgcatctg cgtgttcgaa     4560
ttcgccaatg acaagacgct gggcggggtt tgtgtcatca tagaactaaa gacatgcaaa    4620
tatatttctt ccggggacac cgccagcaaa cgcgagcaac gggccacggg gatgaagcag    4680
ggcatggcgg ccgacgcgct gggctacgtc ttgctgcgt tcgcgacgcg aggctggatg     4740
gccttcccca ttatgattct tctcgcttcc ggcggcatcg ggatgcccgc gttgcaggcc    4800
atgctgtcca ggcaggtaga tgacgaccat cagggacagc ttcaaggatc gctcgcggct    4860
cttaccagcc taacttcgat cactggaccg ctgatcgtca cggcgattta tgccgcctcg    4920
gcgagcacat ggaacgggtt ggcatggatt gtaggcgccg ccctatacct tgtctgcctc    4980
cccgcgttgc gtcgcggtgc atggagccgg gccacctcga cctgaatgga agccggcggc    5040
acctcgctaa cggattcacc actccaagaa ttggagccaa tcaattcttg cggagaactg    5100
tgaatgcgca aaccaaccct tggcagaaca tatccatcgc gtccgccatc tccagcagcc    5160
gcacgcggcg cagcaaaagg ccaggaaccg taaaaaggcc gcgttgctgg cgttttccca    5220
taggctccgc cccctgacg agcatcacaa aaatcgacgc tcaagtcaga ggtggcgaaa      5280
cccgacagga ctataaagat accaggcgtt ccccctgga agctcccctcg tgcgctctcc     5340 tgttccgacc ctgccgctta ccggatacct gtccgccttt ctcccttcgg gaagcgtggc    5400
gctttctcat agctcacgct gtaggtatct cagttcggtg taggtcgttc gctccaagct    5460
gggctgtgtg cacgaacccc ccgttcagcc cgaccgctgc gccttatccg gtaactatcg    5520
tcttgagtcc aacccggtaa gacacgactt atcgccactg gcagcagcca ctggtaacag    5580
gattagcaga gcgaggtatg taggcggtgc tacagagttc ttgaagtggt ggcctaacta    5640
cggctacact agaaggacag tatttggtat ctgcgctctg ctgaagccag ttaccttcgg    5700
aaaaagagtt ggtagctctt gatccggcaa acaaaccacc gctggtagcg gtggtttttt    5760
tgtttgcaag cagcagatta cgcgcagaaa aaaaggatct caagaagatc ctttgatctt    5820
ttctacgggg tctgacgctc agtggaacga aaactcacgt taagggattt tggtcatgag    5880
attatcaaaa aggatcttca cctagatcct tttaaattaa aaatgaagtt ttaaatcaat    5940
ctaaagtata tatgagtaaa cttggtctga cagttaccaa tgcttaatca gtgaggcacc    6000
tatctcagcg atctgtctat ttcgttcatc catagttgcc tgactccccg tcgtgtagat    6060
aactacgata cgggagggct taccatctgg ccccagtgct gcaatgatac cgcgagaccc    6120
acgctcaccg gctccagatt tatcagcaat aaaccagcca gccggaaggg ccgagcgcag    6180
aagtggtcct gcaactttat ccgcctccat ccagtctatt aattgttgcc gggaagctag    6240
agtaagtagt tcgccagtta atagtttgcg caacgttgtt gccattgctg caggcatcgt    6300
ggtgtcacgc tcgtcgtttg gtatggcttc attcagctcc ggttcccaac gatcaaggcg    6360
agttacatga tcccccatgt tgtgcaaaaa agcggttagc tccttcggtc ctccgatcgt    6420
tgtcagaagt aagttggccg cagtgttatc actcatggtt atggcagcac tgcataattc    6480
tcttactgtc atgccatccg taagatgctt ttctgtgact ggtgagtact caaccaagtc    6540
attctgagaa tagtgtatgc ggcgaccgag ttgctcttgc ccggcgtcaa cacgggataa    6600
taccgcgcca catagcagaa ctttaaaagt gctcatcatt ggaaaacgtt cttcggggcg    6660
aaaactctca aggatcttac cgctgttgag atccagttcg atgtaaccca ctcgtgcacc    6720
caactgatct tcagcatctt ttactttcac cagcgtttct gggtgagcaa aaacaggaag    6780
```

```
gcaaaatgcc gcaaaaaagg gaataagggc gacacggaaa tgttgaatac tcatactctt    6840 ccttttcaa tattattgaa gcatttatca gggttattgt ctcatgagcg gatacatatt     6900
tgaatgtatt tagaaaaata aacaaatagg ggttccgcgc acatttcccc gaaaagtgcc    6960
acctgacgtc taagaaacca ttattatcat gacattaacc tataaaaata ggcgtatcac    7020
gaggcccttt cgtcttcaag aattctcatg tttgacagct tatcatcgat aagctgatcc    7080
tcacaggccg cacccagctt ttcttccgtt gccccagtag catctctgtc tggtgacctt    7140
gaagaggaag aggaggggtc ccgagaatcc ccatccctac cgtccagcaa aaaggggggac   7200 gaggaatttg aggcctggct tgaggctcag gacgcaaatc ttgaggatgt tcagcgggag    7260
ttttccgggc tgcgagtaat tggtgatgag gacgaggatg gttcggagga tgggggaattt  7320 tcagacctgg atctgtctga cagcgaccat gaaggggatg agggtgggggg ggctgttgga   7380 ggggggcagga gtctgcactc cctgtattca ctgagcgtcg tctaataaag atgtctattg   7440 atctcttta gtgtgaatca tgtctgacga ggggccaggt acaggacctg gaaatggcct    7500
aggagagaag ggagacacat ctggaccaga aggctccggc ggcagtggac ctcaaagaag    7560 aggggggtgat aaccatggac gaggacgggg aagaggacga ggacgaggag gcggaagacc   7620
aggagccccg ggcggctcag gatcagggcc aagacataga gatggtgtcc ggagacccca   7680
aaaacgtcca gttgcattg gctgcaaagg gacccacggt ggaacaggag caggagcagg    7740
agcgggaggg gcaggagcag gaggggcagg agggaggccg gggtcgagga ggtagtggag    7800
gccggggtcg aggaggtagt ggaggccgcc ggggtagagg acgtgaaaga gccagggggg    7860
gaagtcgtga aagagccagg gggagaggtc gtggacgtgg agaaaagagg cccaggagtc    7920
ccagtagtca gtcatcatca tccgggtctc caccgcgcag gccccctcca ggtagaaggc    7980
catttttcca ccctgtaggg gaagccgatt attttgaata ccaccaagaa ggtggcccag    8040
atggtgagcc tgacgtgccc ccgggagcga tagagcaggg ccccgcagat gacccaggag    8100
aaggcccaag cactggaccc cggggtcagg gtgatggagg caggcgcaaa aaaggagggt    8160
ggtttggaaa gcatcgtggt caaggaggtt ccaacccgaa atttgagaac attgcagaag    8220
gtttaagagc tctcctggct aggagtcacg tagaaaggac taccgacgaa ggaacttggg    8280
tcgccggtgt gttcgtatat ggaggtagta agacctccct ttacaaccta aggcgaggaa    8340
ctgcccttgc tattccacaa tgtcgtctta caccattgag tcgtctcccc tttggaatgg    8400
cccctggacc cggcccacaa cctggcccgc taagggagtc cattgtctgt tatttcatgg    8460 tcttttaca aactcatata tttgctgagg ttttgaagga tgcgattaag gaccttgtta    8520
tgacaaagcc cgctcctacc tgcaatatca gggtgactgt gtgcagcttt gacgatggag    8580
tagatttgcc tccctggttt ccacctatgg tggaaggggc tgccgcggag ggtgatgacg    8640
gagatgacgg agatgaagga ggtgatggag atgagggtga ggaagggcag gagtgatgta    8700
acttgttagg agacgccctc aatcgtatta aaagccgtgt attcccccgc actaaagaat    8760
aaatccccag tagacatcat gcgtgctgtt ggtgtatttc tggccatctg tcttgtcacc    8820
attttcgtcc tcccaacatg gggcaattgg gcatacccat gttgtcacgt cactcagctc    8880
cgcgctcaac accttctcgc gttggaaaac attagcgaca tttacctggt gagcaatcag    8940
acatgcgacg gctttagcct ggcctcctta aattcaccta agaatgggag caaccagcat    9000
gcaggaaaag gacaagcagc gaaaattcac gccccttgg gaggtggcgg catatgcaaa     9060
```

```
ggatagcact cccactctac tactgggtat catatgctga ctgtatatgc atgaggatag    9120
catatgctac ccggatacag attaggatag catatactac ccagatatag attaggatag    9180
catatgctac ccagatatag attaggatag cctatgctac ccagatataa attaggatag    9240
catatactac ccagatatag attaggatag catatgctac ccagatatag attaggatag    9300
cctatgctac ccagatatag attaggatag catatgctac ccagatatag attaggatag    9360
catatgctat ccagatattt gggtagtata tgctacccag atataaatta ggatagcata    9420
tactacccta atctctatta ggatagcata tgctacccgg atacagatta ggatagcata    9480
tactacccag atatagatta ggatagcata tgctacccag atatagatta ggatagccta    9540
tgctacccag atataaatta ggatagcata tactacccag atatagatta ggatagcata    9600
tgctacccag atatagatta ggatagccta tgctacccag atatagatta ggatagcata    9660
tgctatccag atatttgggt agtatatgct acccatggca acattagccc accgtgctct    9720
cagcgacctc gtgaatatga ggaccaacaa ccctgtgctt ggcgctcagg cgcaagtgtg    9780
tgtaatttgt cctccagatc gcagcaatcg cgccctatc ttggcccgcc cacctactta    9840
tgcaggtatt ccccgggtg ccattagtgg ttttgtgggc aagtggtttg accgcagtgg    9900 ttagcgggt tacaatcagc caagttatta caccttatt ttacagtcca aaaccgcagg    9960
gcggcgtgtg ggggctgacg cgtgccccca ctccacaatt tcaaaaaaaa gagtggccac   10020
ttgtctttgt ttatgggccc cattggcgtg gagcccgtt taattttcgg gggtgttaga   10080
gacaaccagt ggagtccgct gctgtcggcg tccactctct ttccccttgt tacaaataga   10140
gtgtaacaac atggttcacc tgtcttggtc cctgcctggg acacatctta ataacccag   10200 tatcatattg cactaggatt atgtgttgcc catagccata aattcgtgtg agatggacat   10260
ccagtcttta cggcttgtcc ccaccccatg gatttctatt gttaaagata ttcagaatgt   10320
ttcattccta cactagtatt tattgcccaa ggggtttgtg agggttatat tggtgtcata   10380
gcacaatgcc accactgaac cccccgtcca aattttattc tggggcgtc acctgaaacc   10440 ttgttttcga gcacctcaca tacaccttac tgttcacaac tcagcagtta ttctattagc   10500
taaacgaagg agaatgaaga agcaggcgaa gattcaggag agttcactgc ccgctccttg   10560
atcttcagcc actgcccttg tgactaaaat ggttcactac cctcgtggaa tcctgacccc   10620
atgtaaataa aaccgtgaca gctcatgggg tgggagatat cgctgttcct taggaccctt   10680
ttactaaccc taattcgata gcatatgctt cccgttgggt aacatatgct attgaattag   10740
ggttagtctg gatagtatat actactaccc gggaagcata tgctacccgt ttagggttaa   10800 caaggggcc ttataaacac tattgctaat gccctcttga gggtccgctt atcggtagct   10860
acacaggccc ctctgattga cgttggtgta gcctcccgta gtcttcctgg gccctggga   10920 ggtacatgtc cccagcatt ggtgtaagag cttcagccaa gagttacaca taaaggcaat   10980
gttgtgttgc agtccacaga ctgcaaagtc tgctccagga tgaaagccac tcagtgttgg   11040
caaatgtgca catccattta taaggatgtc aactacagtc agagaacccc tttgtgtttg   11100
gtcccccccc gtgtcacatg tggaacaggg cccagttggc aagttgtacc aaccaactga   11160
agggattaca tgcactgccc cgaatacaaa acaaaagcgc tcctcgtacc agcgaagaag   11220
gggcagagat gccgtagtca ggtttagttc gtccggcggc ggggc                  11265
```

ENHANCEMENT OF IMMUNE RESPONSE USING TARGETING MOLECULES

This application is a continuation of U.S. Ser. No. 09/402,020 filed Mar. 28, 2000, now abandoned, which is a U.S. national stage of PCT/AU1998/00208 filed Mar. 26, 1998, which claims priority to Australian Patent Applications P05891 filed Mar. 27, 1997 and PP1830 filed Feb. 13, 1998, the disclosures of which are incorporated by reference herein in their entireties.

FIELD OF THE INVENTION

The present invention relates to methods of enhancing the immune response to an immunogen and to compositions for use in these methods. In particular the present invention relates to the use of targeting molecules in DNA and protein vaccination.

BACKGROUND OF THE INVENTION

The ability of direct injection of non-replicating plasmid DNA coding for viral proteins to elicit protective immune responses in laboratory and preclinical models has created increasing interest in DNA immunisation. A useful review of DNA vaccination is provided in Donnelly et al, Journal of Immunological Methods 176 (1994) 145-152, the disclosure of which is incorporated herein by reference.

Intramuscular injection of DNA as a means of vaccination can induce both cellular and humoral responses (1). Studies using reporter proteins demonstrated that muscle cells are the principal target for transfection after intramuscular DNA injection (2). The mechanisms underlying the induction of immune responses after DNA immunisation are unclear. Since myocytes express MHC Class I at low levels and do not constitutively express Class II or costimulatory molecules such as B-7 (3), they appear unlikely candidates for the induction of Ab or CTL responses. It is possible that low level transfection of antigen presenting cells (APCs) occurs at the injection site and these APCs then traffic to lymphoid organs and present the encoded antigen to B and T cells (4) as has been shown after intradermal (5) and biolistic DNA immunisation (6). Alternatively the myocyte may act merely as a source of antigen and priming occurs in the draining lymph node. In the latter case, optimum immune induction would result if the antigen was released from the myocyte by secretion or subsequent to cell damage.

One strategy that has been shown to augment the response to polynucleotide, or DNA, vaccination is the use of sequences encoding cytokines or co-stimulatory molecules (Conry et al, (1996) Gene Therapy 3: 67-74). These investigators showed an increased response when the DNA administered encoded not only the antigen of interest but also for B7-1.

The present inventors investigated the effects of modifying the antigen such that it will be targeted to APC or sites of immune induction. This was shown to not only markedly enhance the immune response but also cause immune deviation.

SUMMARY OF THE INVENTION

In a first aspect the present invention consists in a DNA molecule for use in raising an immune response to an antigen, the DNA molecule including a first sequence encoding a targeting molecule, a second sequence encoding the antigen or an epitope thereof, and optionally a third sequence encoding a polypeptide which promotes dimerisation or multimerisation of the encoded product.

As will be appreciated by those skilled in the art in a number of instances the antigen or epitope encoded by the second sequence will be a polypeptide which promotes dimerisation or multimerisation of the encoded product. As will be understood in such instances the third sequence may be omitted.

In a second aspect the present invention consists in a polypeptide, the polypeptide being encoded by the DNA molecule of the first aspect of the invention.

In a third aspect the present invention consists in a method of raising an immune response in an individual, the method comprising administering to the individual the DNA molecule of the first aspect of the present invention or the polypeptide of the second aspect of the present invention.

There are a wide range of molecules which could be used as targeting molecules. These include ligands which target lymphoid cells (which will either be at or take the Ag to sites of immune induction), lymphoid sites (eg. spleen, lymph nodes, Peyers patches) or APCs directly. Examples of such ligands include, but are not limited to, CD40L, OX40, antibodies to receptors on APCs (eg. DEC 205, CD 23, CD11c, MHC class II), CD28, CTLA4 and L-selectin. It is presently preferred that the targeting molecule is CTLA4 or L-selectin.

In a fourth aspect the present invention consists in a method of deviating the immune response to an antigen in an individual, the method comprising administering to the individual a DNA molecule including a first sequence encoding CTLA4, a second sequence encoding the antigen or an epitope thereof, and optionally a third sequence encoding a polypeptide which promotes dimerisation or multimerisation of the encoded product.

There are many ways of producing dimerisation or multimerisation including tandem duplication and the use of any molecule that normally forms multimers (e.g. Immunoglobulins, CD8, TNF, glutathione s-transferase, zinc finger dimers etc). There are many references in the scientific literature regarding this area. These include Classon B J et al (1992) "The hinge region of the CD8 alpha chain: structure, antigenicity, and utility in expression of immunoglobulin superfamily domains" Int Immunol 4:215-25; Yang J, Moyana T, Xiang J (1995) "A genetically engineered single-chain FV/TNF molecule possesses the anti-tumor immunoreactivity of FV as well as the cytotoxic activity of tumor necrosis factor." Mol Immunol. 32:873-81; Tudyka T, Skerra A (1997) "Glutathione s-transferase can be used as a c-terminal, enzymatically active dimerization module for a recombinant protease inhibitor, and functionally secreted into the periplasm of *Escherichia coli*." Protein Science. 6:2180-2187; Pomerantz J L, Wolfe S A, Pabo CO (1998) "Structure-based design of a dimeric zinc finger protein" Biochemistry 37:965-970; and Whiteheart S W, Rossnagel K, Buhrow S A, Brunner M, Jaenicke R, Rothman J E (1994) "N-ethylmaleimide-sensitive fusion protein: a trimeric ATPase whose hydrolysis of ATP is required for membrane fusion." J Cell Biol 126:945-54. The disclosure of these references and the other references referred to in this application are included herein by cross-reference.

As will be appreciated by those skilled in the art in the constructs of the present invention the first, second and third DNA sequences may be in any particular order. It is presently preferred that the order is first, third then second.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

DETAILED DESCRIPTION OF THE INVENTION

In order that the nature of the present invention may be more clearly understood preferred forms thereof will now be described with reference to the following examples and Figures in which:

FIG. 1. Secretion of ΔIg, CTLA4Ig and L-SELIg proteins from NIT transfectants. NIT cells were transfected with the pRep10::CD5L-hIg, pRep7::mCTLA4-hIg and pRep10::hL-SEL-hIg expression plasmids. Secreted protein was purified on immobilised protein A and samples run by SDS PAGE under reducing and non-reducing conditions.

FIG. 2. hIg specific IgG responses in DNA immunized mice. Sera were obtained from BALB/c mice immunized with pRep10::CD5L-hIg, pRep7::mCTLA4-hIg and pRep10::hL-SEL-hIg at the indicated times post immunisation and stored at −20° C. until assayed for hIg specific IgG in an ELISA. Titres were defined as the highest dilution to give a 0.2 OD at 450 nm. Results are expressed as the mean of the log titre ±SEM from 5 mice in each group. Normal mouse sera and hyperimmune mouse sera served as the negative and positive controls respectively.

FIG. 3. hIg specific IgG subclass responses in DNA immunized mice. A. Sera were obtained from BALB/c mice immunized with pRep10::CD5L-hIg, pRep7::mCTLA4-hIg and pRep10::hL-SEL-hIg at 8 weeks post immunisation and stored at −20° C. until assayed for hIg specific IgG1, IgG2a or IgG2b in an ELSA. Titres were defined as the highest dilution to reach an OD of 0.2 at 450 nm. Results are expressed as the mean of the log titre ±SEM from 5 mice in each group. B. The log IgG1 titre for each mouse was divided by the corresponding log IgG2a titre to obtain a log IgG1: log IgG2a ratio. Results are expressed as the mean ±SEM from 5 mice in each group.

FIG. 4. hIg specific IgG subclass responses in soluble protein immunized mice. Sera were obtained from BALB/c mice immunized with 5 μg of hIg or 5 μg of CTLA4Ig protein in 100 μl of PBS, 2 weeks post immunisation and assayed for hIg specific IgG in an ELSA. Titres were defined as the highest dilution to reach an OD of 0.2 at 450 nm. Results are expressed as the mean of the log titre ±SEM from 5 mice in each group.

FIG. 5. hIg specific IgG subclass responses in CTLA4Ig DNA immunized mice. Sera were obtained from BALB/c mice immunized with the indicated dose of pRep7::mCTLA4-hIg 2 weeks post immunisation and assayed for hIg specific IgG1, IgG2a or IgG2b in an ELSA. Titres were defined as the highest dilution to reach an OD of 0.2 at 450 nm. Results are expressed as the mean of the log titre ±SEM from 5 mice in each group.

FIG. 6. OVA specific IgG and IgG subclass responses after co-injection of DNA. Sera were obtained from BALB/c mice immunized with pRep10::hL-SEL-hIg and pCI-OVA or pRep7::mCTLA4-hIg and pCI-OVA at 4 weeks post immunisation and assayed for OVA specific IgG (A) or IgG1, IgG2a or IgG2b (B) in an ELSA. Titres were defined as the highest dilution to reach an OD of 0.2 at 450 nm. Results are expressed as the mean of the log titre ±SEM from 5 mice in each group.

FIG. 7 Shows stimulation index with hIg, Lsel-hIg and CTLA4-hIg (▦ HuIg 1 mg/ml; ▪ HuIg 1 mg/ml; ▪ HuIg 1 mg/ml)

FIG. 8. Shows anti-ovalbumin IgG titres with various constructs (▪ 2 weeks; ▪ 4 weeks)

FIG. 9. Shows anti-OVA IgG titres with pCI::mCTLA4-g3h-OVA and pCI::mCTLA4-hIg-OVA FIG. 10. Groups of 5 Balb/c mice were vaccinated intramuscularly on days 0 and 28 with 0.1 mg of pCI::mCTLA4-hIg-45W (black circles) or pCI::CD5L-hIg-45W (grey circles). Mice were bled on days 0, 7, 14, 28, 35 and 42. Sera was assayed for anti-45w antibodies by ELISA using recombinant 45W(His)6. The Student's t-test was used to compared the two groups and the probability values (P) for the two vaccines at each time point are shown at the top of the figure.

FIG. 11. Groups of 5 Balb/c mice were vaccinated either intraperitoneally with 20 μg of recombinant 45w(His)6 protein (grey circles) in Freund's complete adjuvant or intramuscularly with 0.1 mg pCI::mCTLA4-hIg-45W (black circles) in 0.1 ml of saline. Mice were bled on days 0, 2, 5, 8, 14 and 28 post-vaccination and anti-45w antibodies measured by ELISA using 45W(His)6 protein. The responses were compared by Student's t-test and were different at day 8 ($p<0.05$).

FIG. 12. Shows % survival of mice following challenge with *Plasmodium chabaudi adami* DS (▦ pCI::CD5LhIg-AMA; ▪ pCI::CTLA4-hIg-AMA; ▪ pCI::CTLA4-hIg).

Figure 17:
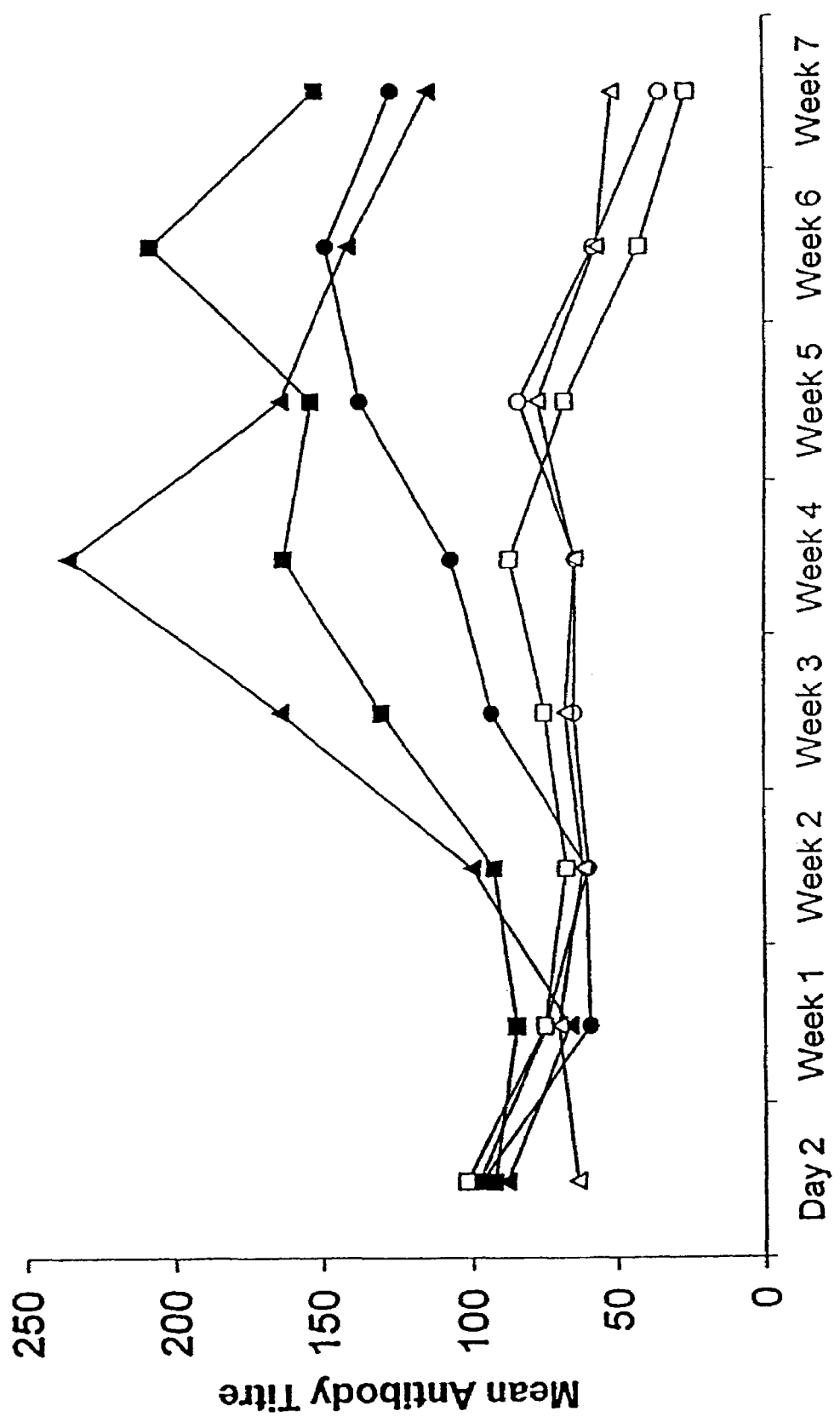

FIG. 17. Kinetics of induction of the anti-hIg antibody titres post-immunisation. Filled symbols represent plasmids containing hIg: filled squares (pCI::bCTLA4-hIg-ΔPLD), filled circles (pCI::CD5L-hIg-ΔPLD), filled triangles (pCI::bCTLA4-hIg). Open symbols represent control animal groups not injected with hIg in any form: open circles (pCI::ΔPLD), open squares (Unvaccinated controls) and open triangles (Glan-Vac).

Figure 18:
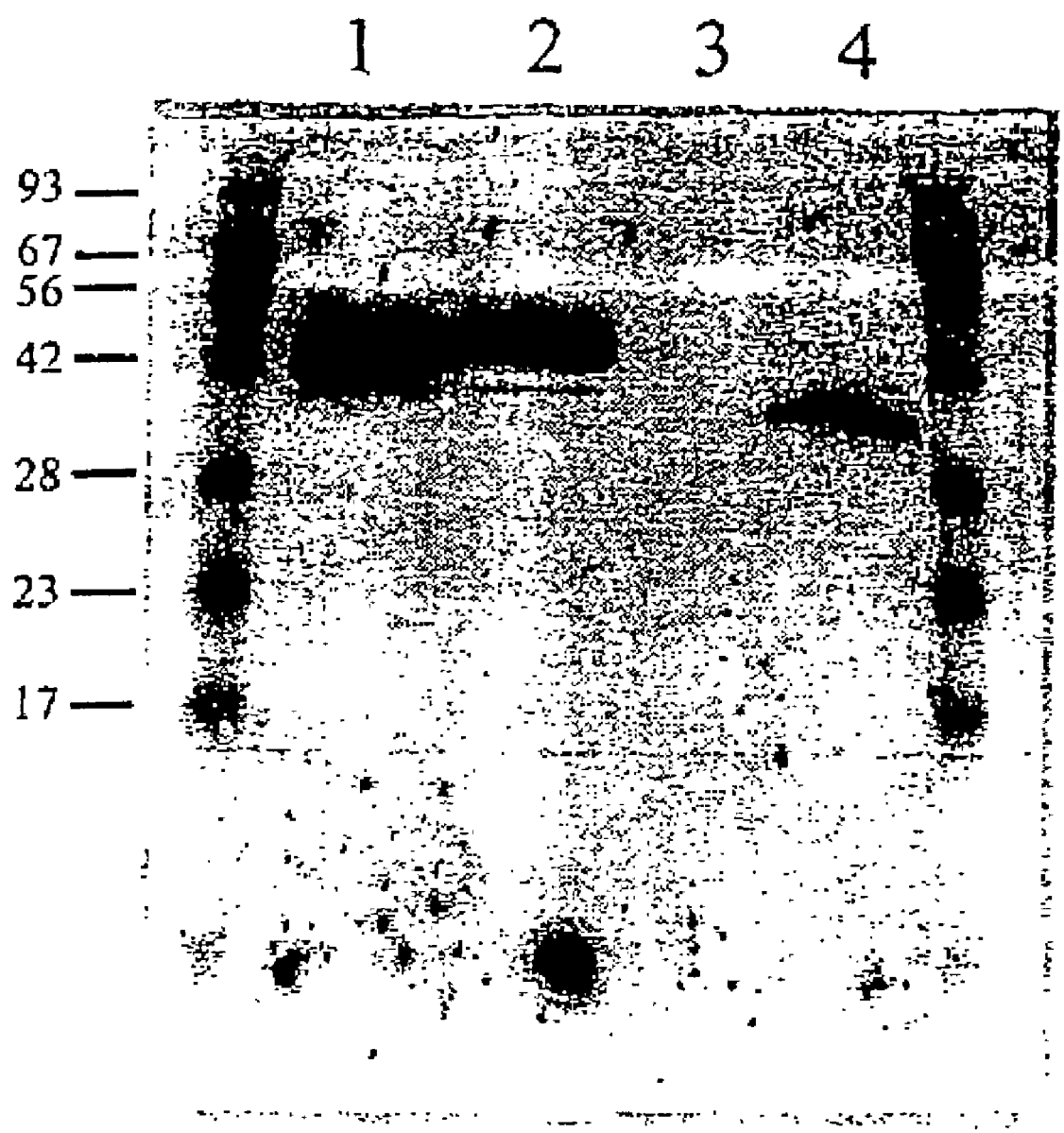

FIG. 18. Western Blot of PLD expressed by eukaryotic and prokaryotic cells. Lane 1-3. Supernatant from Cos-m6 cells transfected with pCI::PLD (lane 1), pCI::ΔPLD (lane 2) and pCI alone (lane 3). Lane 4. Cell filtrate containing PLD expressed from *Corynebacterium pseudotuberculosis*

Figure 19:
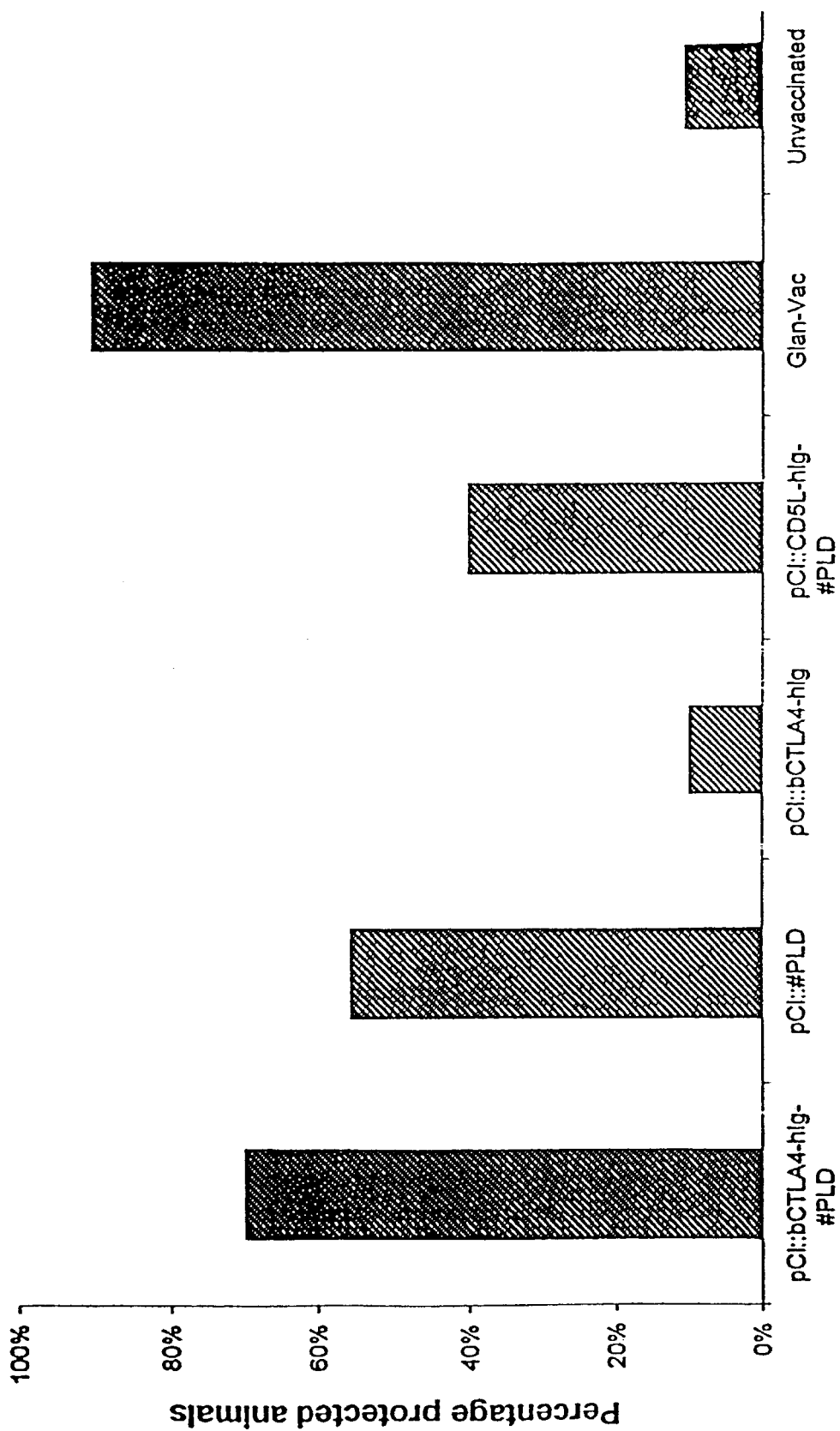

FIG. 19. Protection from challenge with *Corynebacterium pseudotuberculosis*. Percentage of the animals protected from challenge by $10^6$ CFU of *Corynebacterium pseudotuberculosis* injected just above the coronet. Protection was defined as the animal not having abscesses in any of the following lymph nodes: popliteal, inguinal and prefemoral both left and right.

Figure 20:
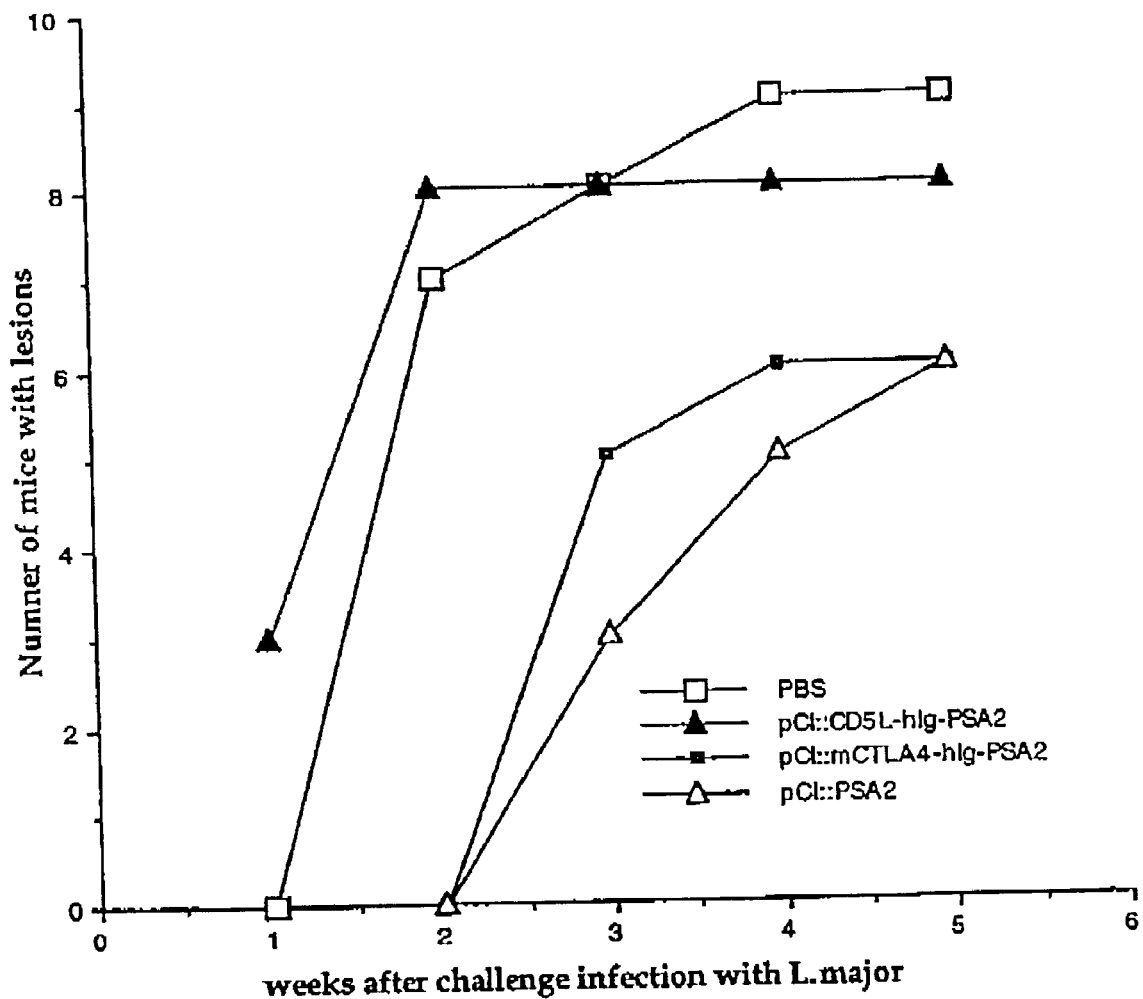

FIG. 20 Shows number of mice with lesions at various time points after challenge with *L. major* (☐ PBS; ▲ pCI::CD5L-hIg-PSA2; ▪ pCI::mCTLA4-hIg-PSA2; Δ pCI::PSA2)

EXAMPLE 1

Materials and Methods

Mice

Female mice (BALB/c, CBA and C57B1/6) aged 6 to 8 weeks were used in all experiments. Mice were maintained in SPF conditions.

Plasmids and Immunisations

Expression plasmids were constructed to produce secreted forms of the Fc fragment of human IgG1 (ΔIg) by using the Cd5 leader sequence (CD5L) either alone or fused with murine CTLA4 (mCTLA4Ig) or human L-selectin (hL-SELIg) under the control of the RSV promoter in the Rep7 or Rep10 vectors (these vectors differ only in the direction of the multiple cloning site, Invitrogen, San Diego, Calif., USA). The sequence of pREP7::CTLA4-hIg is shown in Sequence ID No. 1-Promoter RSV: 13-640, CTLA4-hIg: 703-2462. The constructs were obtained from plasmids given by Drs. P. Lane (Basel Institute, Switzerland), B. Seed (Massachusetts General Hospital, Boston, USA) and D. L. Simmons (Institute of Molecular Medicine, Oxford, UK). The following constructs were generated:

pRep10::CD5T-hIG
pRep7::mCTLA4-hIg
pRep10::hLSEL-hIg

Plasmids for injection were prepared from *E. coli* by PEG precipitation as described (7) except that volumes of Solution I, II and III were adjusted such that pellets were resuspended in 50 mL of Solution I for each Litre of broth media used. Endotoxin was removed from plasmid preparations by four Triton X-114 phase separations (8) and DNA was stored at −20° C. in normal saline until injected. The resultant plasmid preparations contained less than 10 IU endotoxin per mg of plasmid DNA as determined by the limulus amoebocyte lysate assay (QCL-1000 BioWhittaker, Walkersville, Md., USA). Mice received 100 µg of plasmid DNA in both quadriceps or intradermally at the base of the tail on day 0 and 14 of each experiment.

Antibody Assays

Microtitre plates (Dynatech, Chantilly, VI., USA) were coated with human Ig (hIg) protein (Intragam, CSL, Parkville, Australia; 10 µg/ml in PBS) by overnight incubation at 4° C. and washed four times with PBS to remove unbound antigen. Plates were incubated with serially diluted sera in blocking buffer (5% milk powder in PBS) overnight at 4° C. After washing 5 times with PBS to remove unbound Ab, plates were incubated with peroxidase conjugated anti-mouse IgG, IgG1, IgG2a or IgG2b antibodies (Southern Biotechnology, Birmingham, Ala., USA) diluted in blocking buffer. After washing five times with PBS, the amount of bound Ab was determined by addition of substrate solution (0.1 mg/ml 3,3,5,5-tetra methylbenzidine (T2885, Sigma St. Louis, Mo., USA) 0.03% $H_2O_2$ in 0.1M Na acetate pH 6.0). The reaction was stopped with 1M $H_2SO_4$ and the OD read at 450 nm. Titres were defined as the highest dilution to reach an OD of 0.2.

To calibrate the IgG subclass ELISA, plates were coated with IgG1, IgG2a or IgG2b from mouse myelomas (10 µg/ml in 0.5 times PBS) overnight at 4° C., washed 3 times with PBS and then incubated with serially diluted anti-mouse IgG subclass HRP conjugated Ab. The dilution of each anti-mouse subclass Ab which gave identical absorbances in the ELISA were used subsequently.

Results and Discussion

Figure 1:
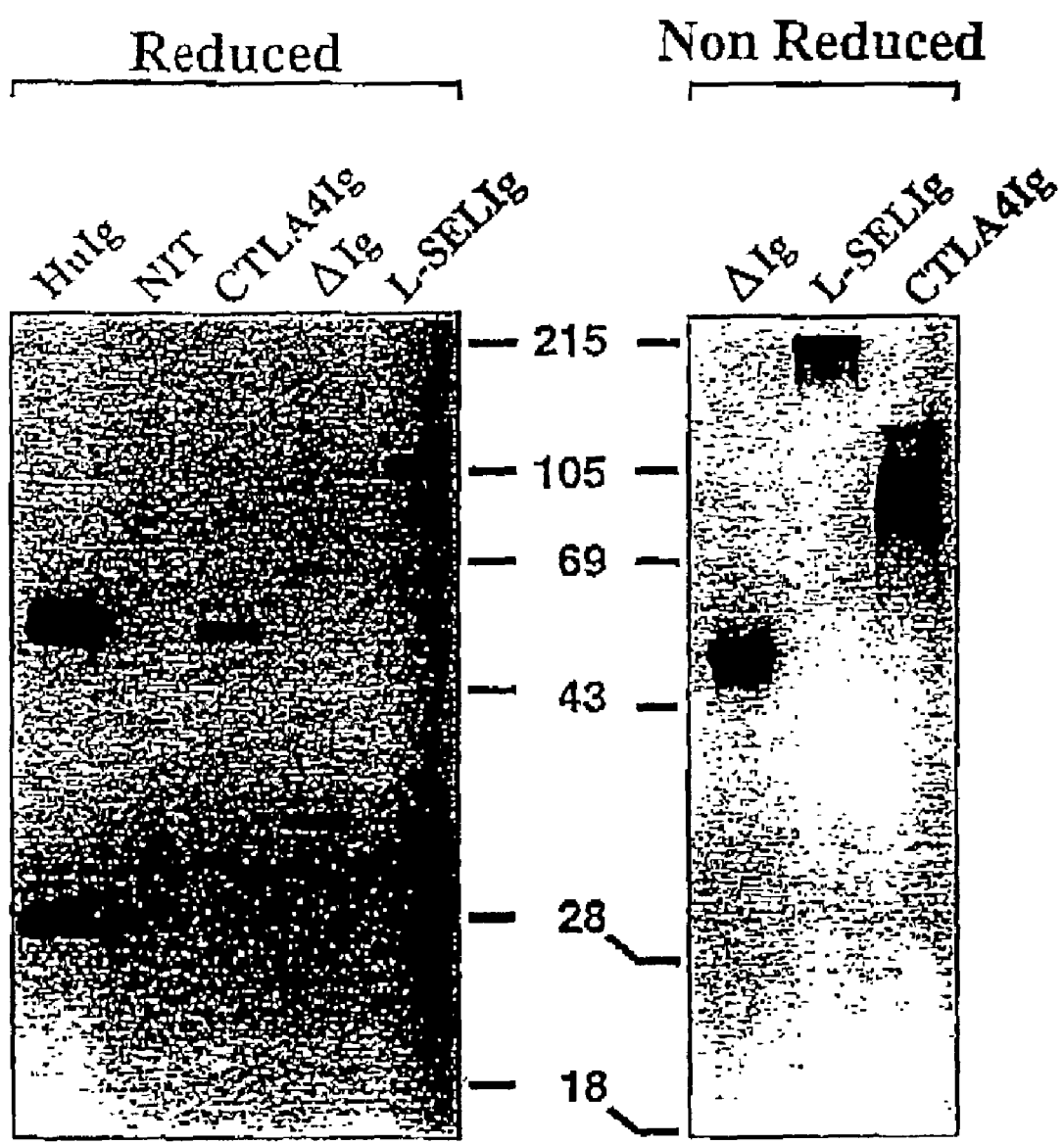
Figure 2:
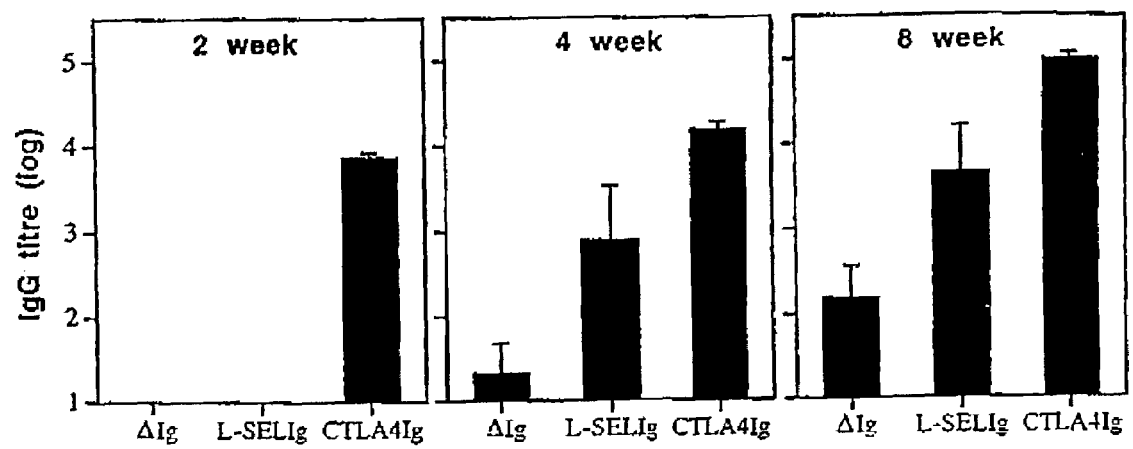

Expression plasmids were constructed to produce secreted forms of the human IgG1 heavy chain alone (pRep10::CD5L-hIg) or fused with CTLA4 (pRep7::mCTLA4-hIg) or L-selectin (pRep10::hLSEL-hIg). Cells transfected with these plasmids secreted the three molecules as disulphide linked dimers of expected size (FIG. 1). Like others (1) we were unable to detect in vivo protein expression by western blotting of muscle homogenates and or of protein A purified material from sera of B-cell deficient immunized mice (data not shown). However, the ability to detect immune responses in immunized mice is indicative of in vivo expression. No immune responses to human Ig were detected in unimmunised or mice receiving vector only (data not shown). However, mice immunized with pRep10::CD5L-hIg, pRep10:: hL-SEL-hIgΔIg or pRep7::mCTLA4-hIg had markedly different responses (FIG. 2). Responses in pRep7::mCTLA4-hIg immunized mice were more rapid and of greater magnitude at all three time points: 2, 4 and 8 weeks (FIG. 2). At 4 weeks both the pRep7::mCTLA4-hIg and pRep10::hLSEL-hIg immunized mice had 1000 and 100 fold higher IgG responses than pRep10::CD5L-hIg controls respectively. The differences observed were not attributable to any adjuvant effects of endotoxin, because Triton X-114 was used to remove endotoxin (8) so that the levels were <10 IU/mg plasmid DNA. Similar results have been achieved in 3 experiments using BALB/c and CBA mice (data not shown).

Figure 3:
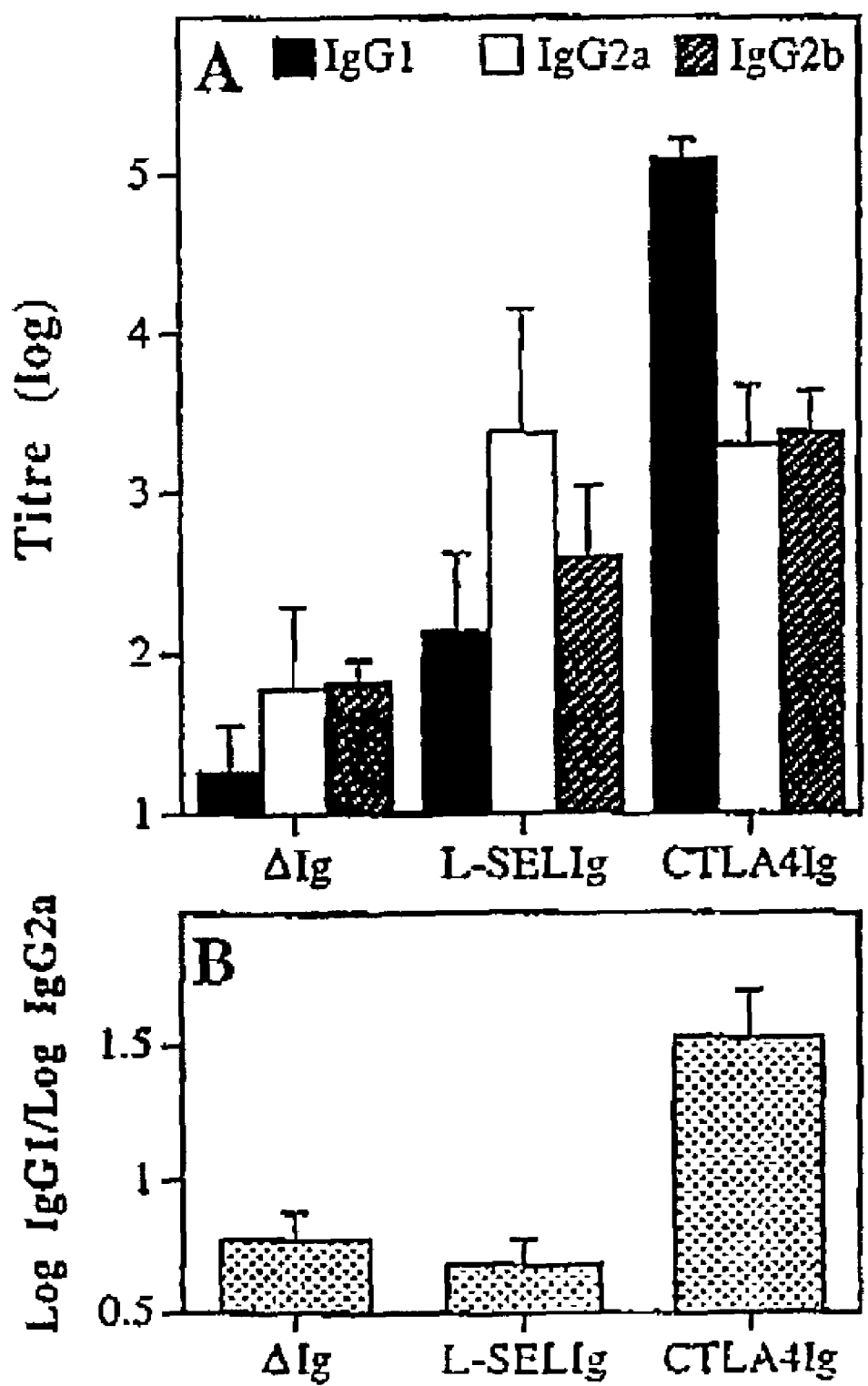
Figure 4:
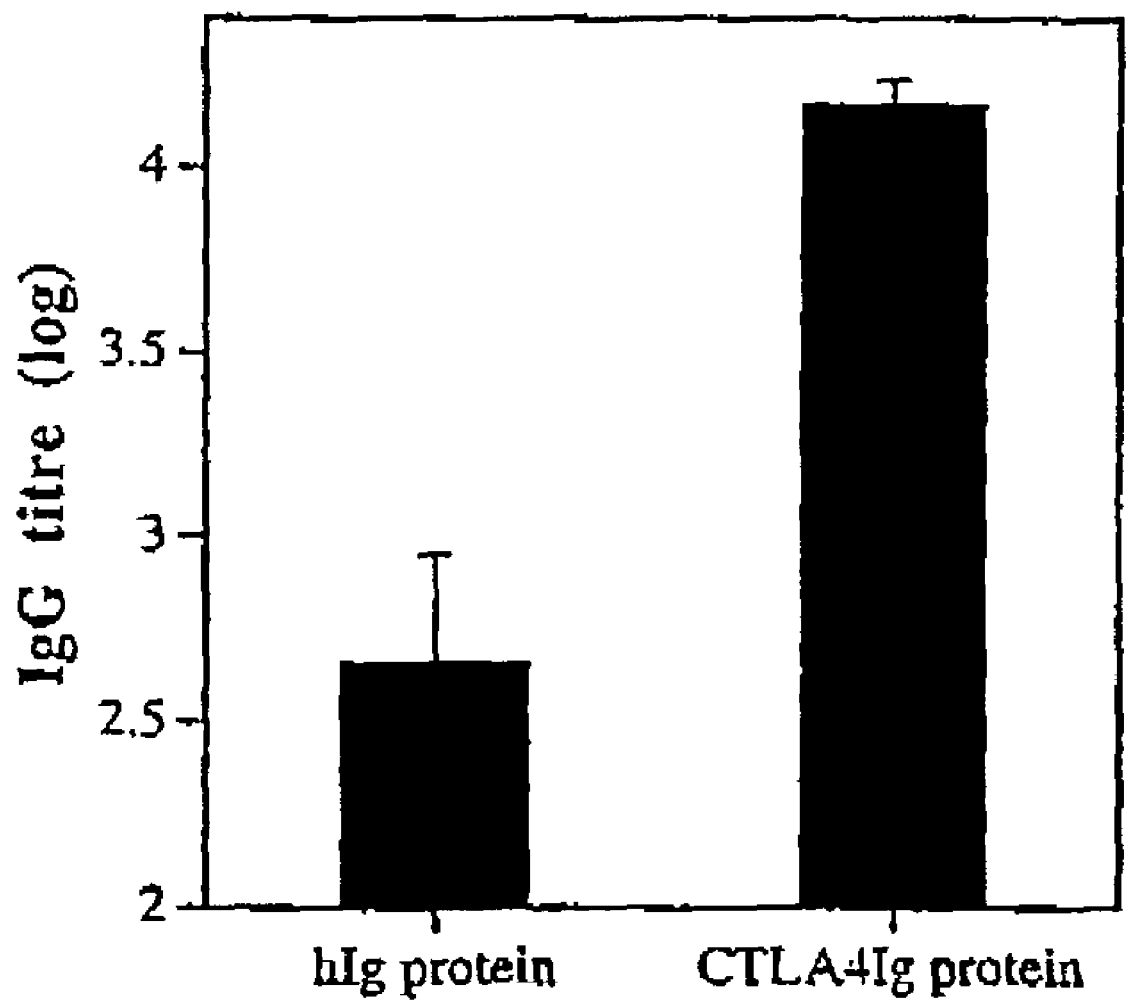
Figure 5:
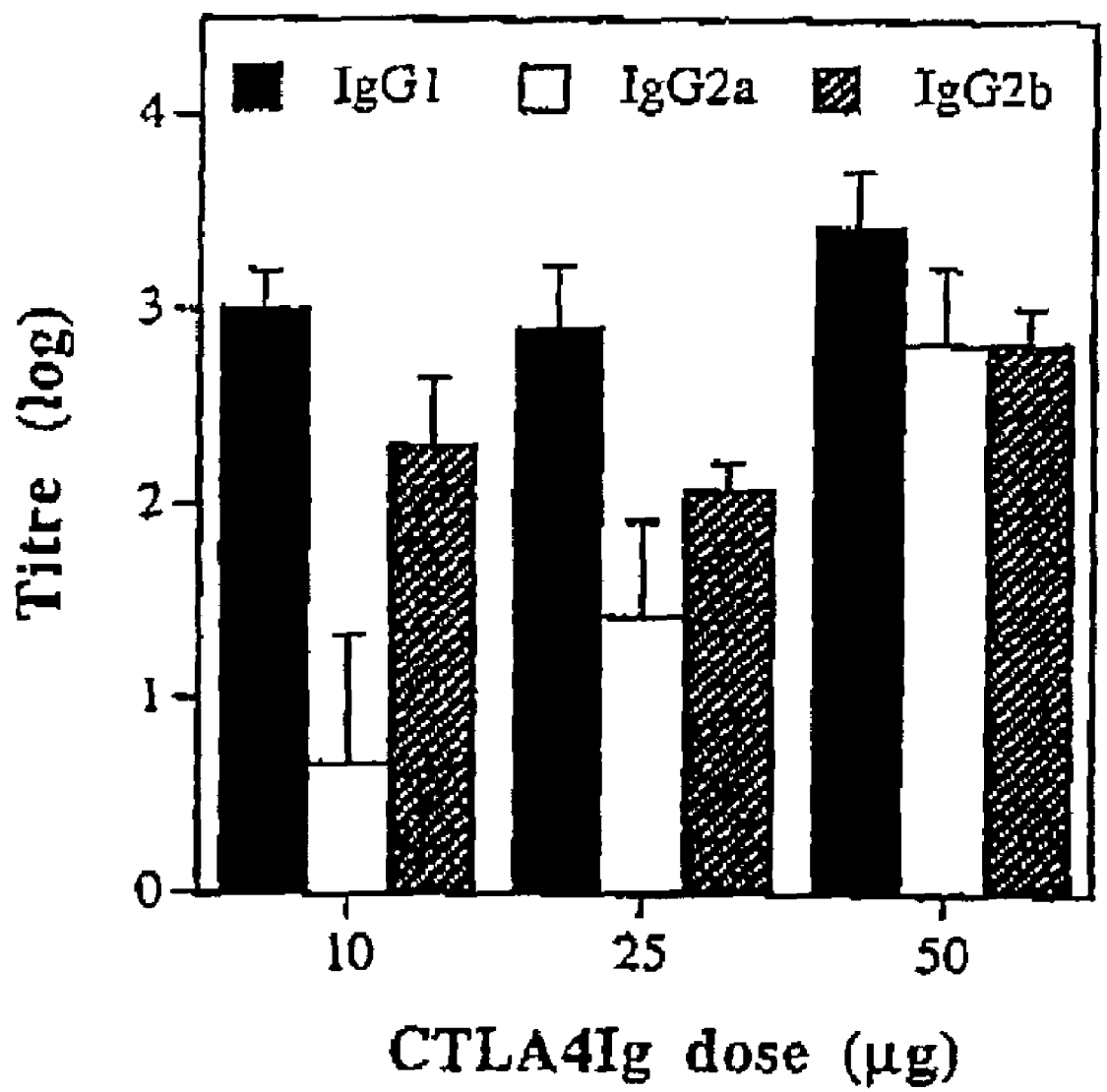

The response in all mice to pRep10::CD5L-hIg was dominated by IgG2a (FIG. 3), which mimics a viral infection, and has been reported for other antigens after DNA immunisation (9, 10). The IgG subclass response in pRep10::hLSEL-hIg immunized mice was similar (although greater) to pRep10:: CD5L-hIg controls whereas the pRep7::mCTLA4-hIg response was deviated to an IgG1 dominance (FIG. 3B). The possibility that the differences in Ab responses was due to dose was unlikely since all constructs were made with identical plasmid backbone and mice immunized with soluble CTLA4Ig protein (FIG. 4) had higher Ab responses than those receiving an equivalent dose of hIg. Also, to determine if the IgG1 dominance of the response to pRep7::mCTLA4-hIg was due to dose we immunized mice with different amounts of pRep7::mCTLA4-hIg so that mice with total IgG antibody levels could be compared to that of pRep10:: hLSEL-hIg (FIGS. 2 and 3). The IgG1 predominance was found at all doses of pRep::mCTLA4-hIg (FIG. 5).

Figure 6:
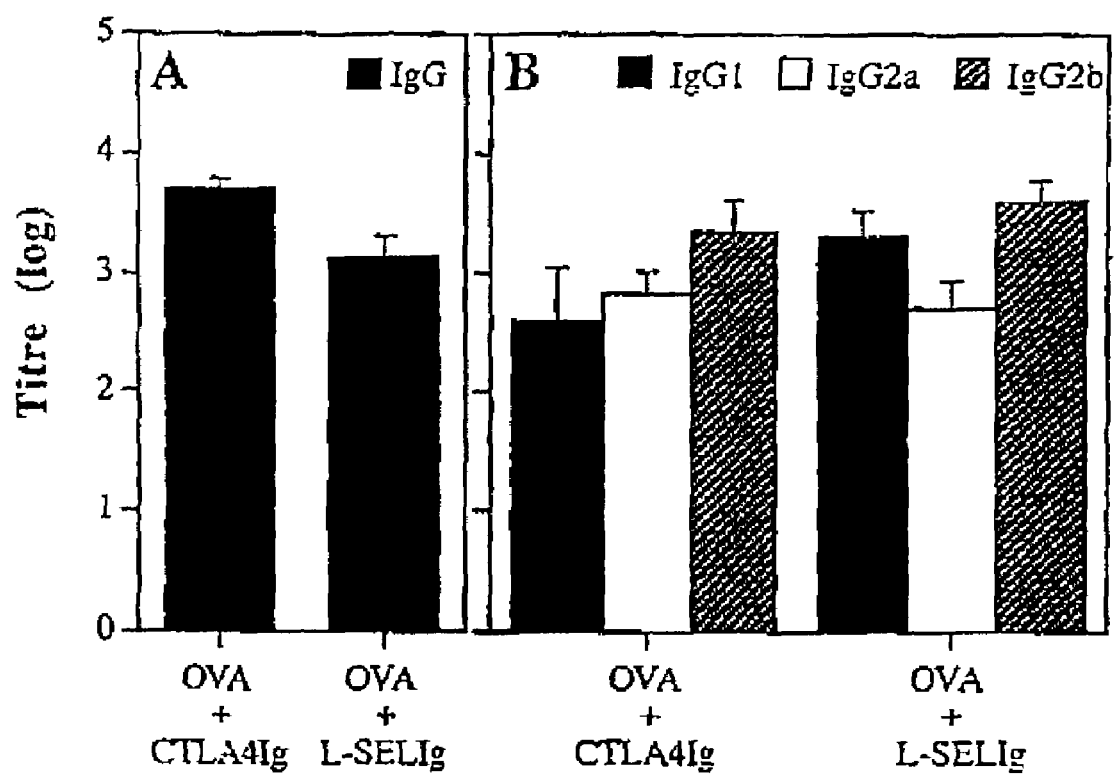

Work with CTLA4 has demonstrated it can bind to B-7 and block co-stimulation which reduces the response to other immunogens (11). A non-specific immunomodulatory effect of CTLA4 was unlikely for several reasons. Firstly, CTLA4Ig protein at least in high doses (and hence B-7 is blocked) has been ascribed immunosuppressive properties not immunostimulating ones (11) as we found for DNA and protein immunisations. Furthermore, mice co-injected with CTLA4Ig and DNA encoding ovalbumin (pCI-OVA) had similar ovalbumin specific IgG and IgG subclass titres to control mice (FIG. 6) indicating that there was not any immunosuppressive effect of CTLA4.

EXAMPLE 2

Use of Targeting Ligand to Augment T Cell Proliferative Responses and Requirement for Dimerisation Introduction In Example 1 there is a demonstration that Ab levels to a model DNA vaccine could be enhanced when antigen was fused with the targeting ligands CTLA4 or L-selectin.

The hIg component would ensure dimerisation which we thought would be favourable because in general, binding of ligands to receptors is stronger when dimers are used. However, it was unclear in this system if dimerisation of the antigen targeting ligand fusion proteins was necessary for increased immune responses. To determine if the enhanced Ab response generated by antigen targeting vectors encoding proteins was dependent upon dimer formation, Ab responses were compared to immunisation with plasmid encoding monomeric antigen targeting ligand fusion proteins. The hIg component of the vectors was replaced with coding sequence for another model antigen that would not form dimers (ovalbumin; OVA).

Materials and Methods

Female mice aged 6 to 8 weeks were used in all experiments and maintained in SPF conditions.

After PCR amplification to include an Mlu I restriction enzyme recognition sequence, the OVA cDNA (bp 470-1170) was inserted behind the human immunoglobulin Fc (hIg) gene via a 4 amino acid glycine linker at the Nsi I site. These vectors would form dimers due to the interchain disulfide bonds of hIg and are represented by an hIg-OVA suffix. A targeting vector that would not form dimers was obtained by direct fusion of the cDNA from OVA to the cDNA of CTLA4 (pCI::mCTLA4-OVA) or to the leader sequence of CD5 as a control (pCI::CD5L-OVA). After PCR amplification to include Hind III and Nsi I restriction sites the entire hIg component of pCI::mCTLA4-hIg-OVA was replaced with the human IgG3 hinge region (a gift from Dr Y Akahori, Japan) to form pCI::mCTLA4-g3h-OVA. Plasmids for injection were prepared from *E. coli* with endofree QIAGEN maxi kits according to the manufacturer's instructions and stored at −20° C. in normal saline until injected. Mice received 50 µg of plasmid DNA in 100 µl normal saline i.m. in both quadriceps at day 0 of each experiment.

The proliferation of $2 \times 10^5$ splenocytes was determined by a standard 5 day $^3$H-thymidine uptake protocol at 6 weeks post initial immunisation. The mean stimulation index was calculated as the cpm with antigen/cpm splenocytes alone.

Microtitre plates (NUNC, Maxisorb) were coated with OVA protein (A-5503, Sigma, St. Louis, Mo.; 10 µg/ml in PBS) by overnight incubation at 4° C. and washed four times with PBS to remove unbound antigen. Plates were incubated with serially diluted sera in blocking buffer (1% casein in PBS) overnight at 4° C. After washing 5 times with PBS to remove unbound Ab, plates were incubated with peroxidase conjugated anti-mouse IgG (Southern Biotechnology, Birmingham, Ala.) diluted in blocking buffer. After washing five times with PBS, the amount of bound Ab was determined by addition of tetramethylbenzidine substrate solution. The reaction was stopped with 1M $H_2SO_4$ and the OD read at 450 nm. Titres were defined as the highest dilution to reach an OD of 0.2.

Results and Discussion

Figure 7:
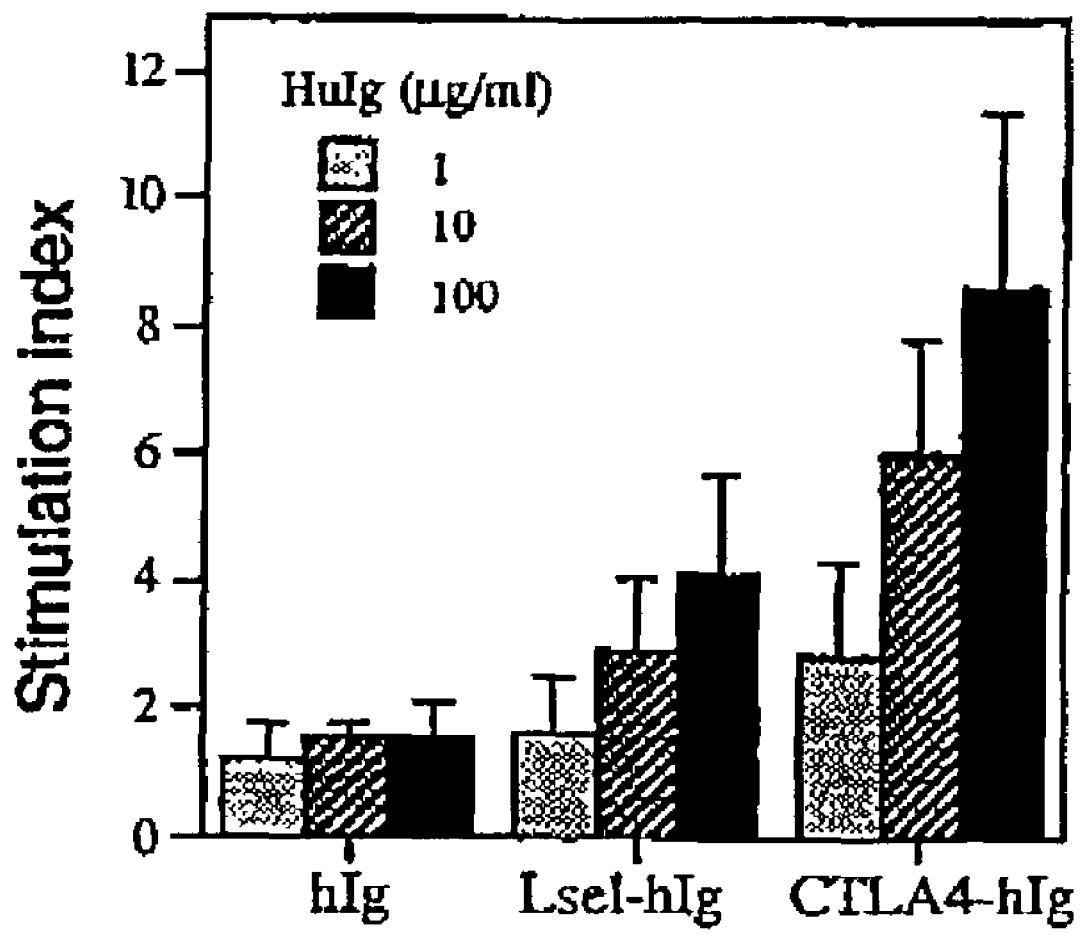

The proliferation splenocytes was determined by a standard 5 day 3H-thymidine uptake protocol at 6 weeks post initial immunisation (FIG. 7). The stimulation index was calculated as the cpm with antigen/cpm splenocytes alone. The mean ±SD from 3 mice in each group is shown after incubation with three different antigen concentrations. Mice immunized with the DNA constructs pCI::mCTLA4-hIg and pCI::Lsel-hIg had 8 and 3 fold higher T cell proliferative responses than controls (pCI::CD5L-hIg) respectively. This data suggested that the targeting of antigen was having an enhancing effect on T cell activation.

Figure 8:
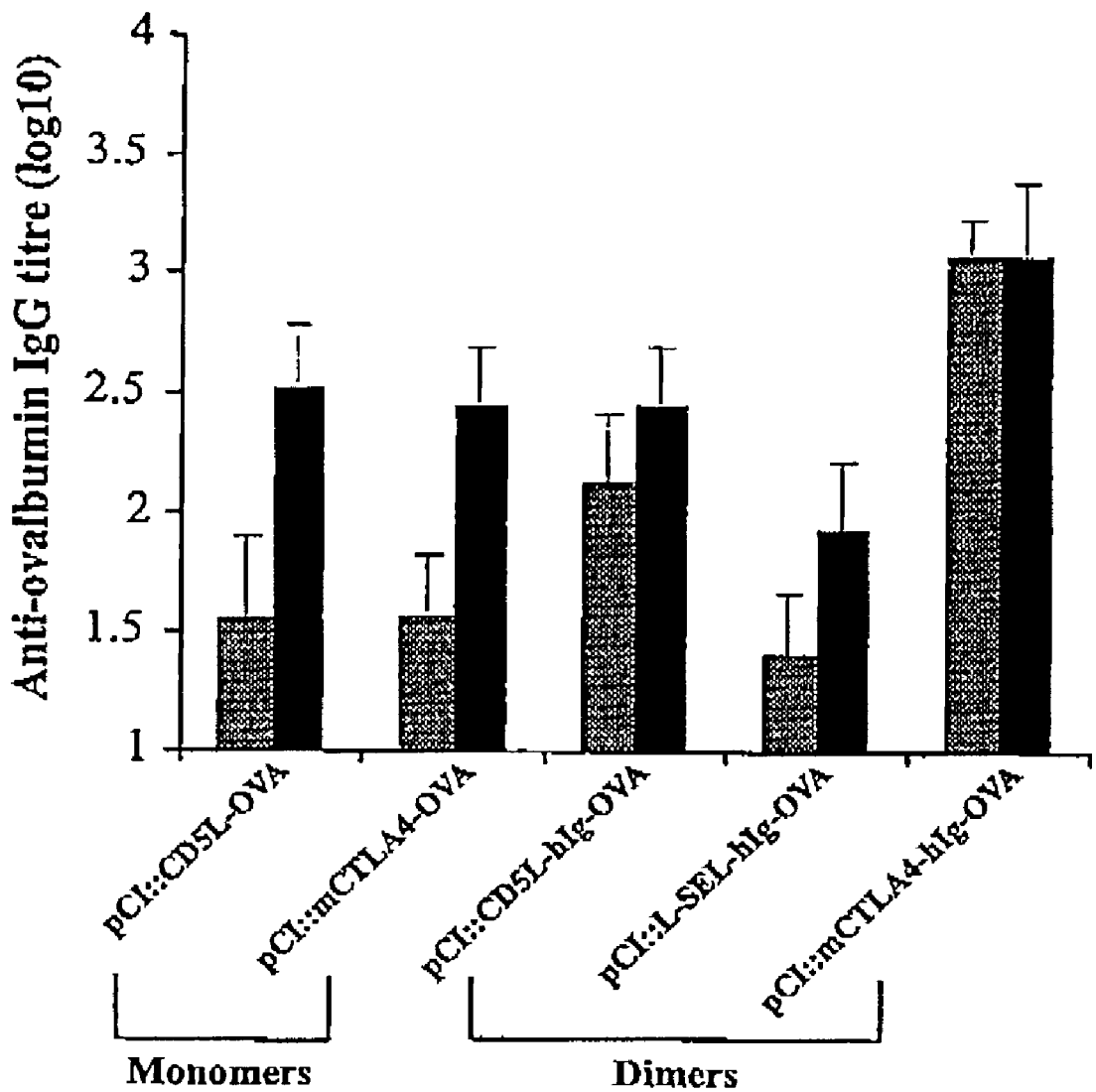

Groups of 8 mice were immunized with DNAs expressing the monomeric targeting vector pCI::mCTLA4-OVA, the monomeric control pCI::CD5L-OVA, or the dimeric vectors pCI::CD5L-hIg-OVA (control), pCI::Lsel-hIg-OVA or pCI::CTLA4-hIg-OVA on day 0 and bled 2 and 4 weeks post immunisation. The OVA specific IgG levels were determined by ELISA. The results obtained at 2 and 4 weeks post immunisation are illustrated in FIG. 8 (2 weeks; hatched columns, 4 weeks; solid columns). There was no difference in Ab levels at 2 or 4 weeks between the mice immunized with pCI::CD5L-OVA or pCI::mCTLA4-OVA monomeric DNA vectors. The highest Ab responses were obtained with the pCI::mCTLA4-hIg-OVA vector, which forms dimers, compared to the monomeric (pCI::CD5L-OVA) or dimeric (pCI::CD5L-hIg-OVA) controls.

Surprisingly, the pCI::Lsel-hIg-OVA immunized mice had the poorest responses at both time points. This data is in contrast to the enhanced responses to hIg when fused with L-selectin alone. The observation that the responses obtained with pCI::Lsel-hIg-OVA were similar in magnitude to those obtained with the monomeric antigen fusions suggests that the fusion of OVA (or other antigens) to Lsel-hIg may interfere with the efficiency of binding of L-selectin to its ligand (e.g. by interfering with dimerisation, by allosteric effects or by conformational changes to L-selectin). Alternative ways of fusion should be investigated.

Figure 9:
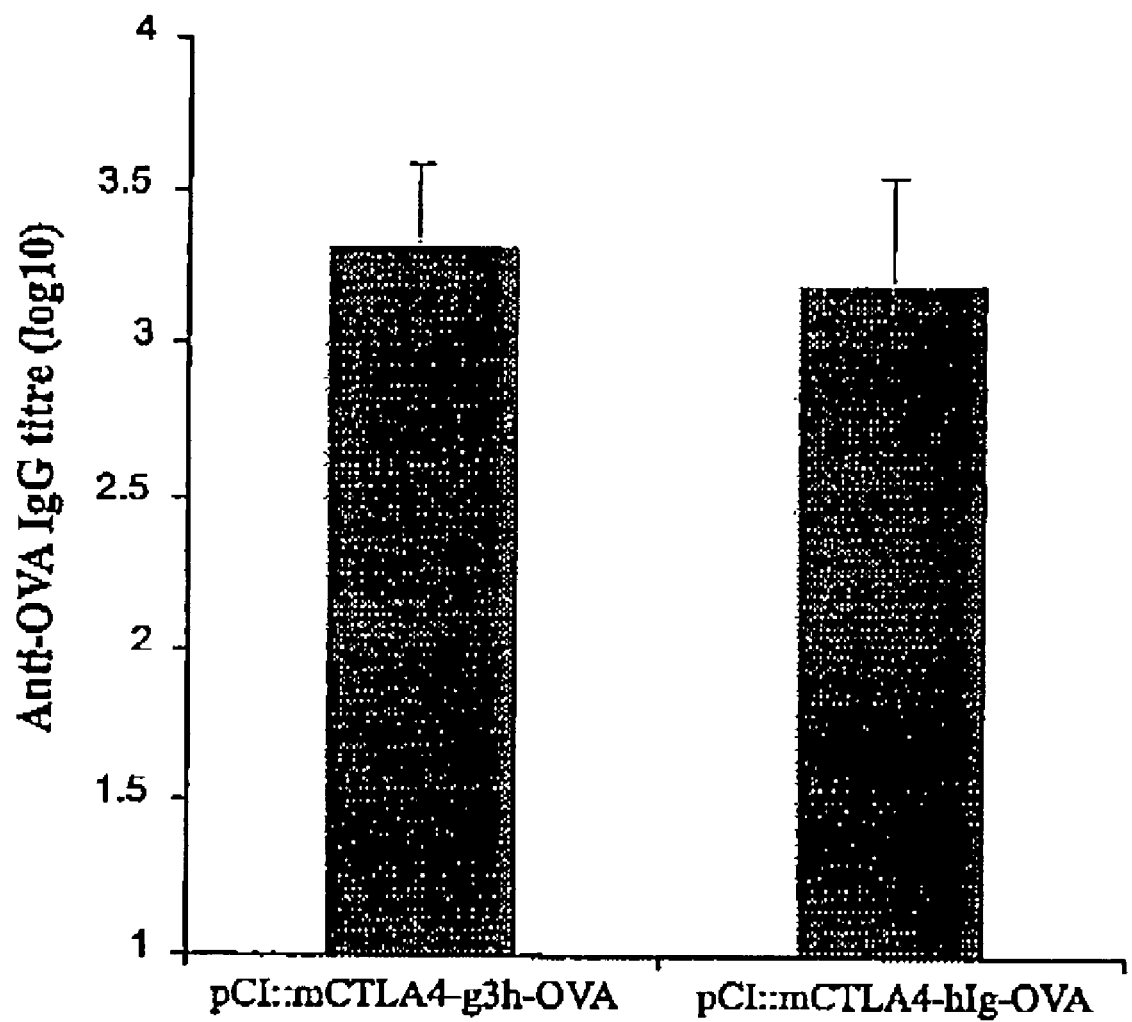

Overall, these results suggest that for effective antigen targeting the inclusion of a molecule such as hIg that facilitates dimerisation is essential unless the antigen itself facilitates dimerisation or multimerisation. This data was obtained using the hinge, CH2 and CH3 domains of human IgG1. The dimerisation of hIg is facilitated by disulfide bonds between cysteine residues in the hinge domains. To determine if another molecule that would also facilitate dimerisation could replace the hIg component, the hinge region of human IgG3 was used to link mCTLA4 with OVA. Groups of 8 mice were immunized with DNAs expressing the targeting vectors pCI::mCTLA4-hIg-OVA or pCI::mCTLA4-g3h-OVA. At 2 weeks post immunisation sera was collected and shown to contain similar levels of anti-OVA antibodies (FIG. 9). Therefore, this suggests that it may be possible to reduce the hIg component of the antigen targeting vectors to a hinge region alone or replace the hIgG1 component with another immunoglobulin hinge region, another molecule or part thereof such as the hIgG3 hinge to facilitate dimerisation. This would be of particular applicability when the targeting ligand is L-selectin or another molecule that does not dimerise or is structurally compromised by fusion of antigen via hIg.

Example 1 demonstrated an increased immune responses to hIg after DNA and protein immunisation was obtained with targeting ligand-hIg fusions. The following Examples were conducted to determine if antigens other that hIg could be used for increased immune responses. These data were obtained by the addition of antigens to the C-terminus of hIg which could facilitate dimer formation as was found with hIg alone. A gly-gly-gly-gly-thr spacer was introduced between hIg and the antigens. Whilst these constructs have been used it will be appreciated that responses may be improved by routine optimisation. This optimisation may involve modification of the constructs as envisaged within the present invention eg different targeting molecules, different sequences which facilitate multimerisation, different linkers etc.

EXAMPLE 3

Use of CTLA4 to Accelerate Immune Responses Against the Host Protective Antigen of *Taenia ovis* Known as 45W Introduction The 45W antigen is a putative membrane glycoprotein present in, or underlying the tegument of, the *Taenia ovis* oncosphere. *T. ovis* is a pathogen of sheep which causes commercial losses of mutton and wool in New Zealand and other important sheep growing countries. Early immunisation studies using 45W protein partially purified from *T. ovis* revealed that it was a promising vaccine antigen. Subsequent field trials using recombinant forms of 45W, expressed in *Escherichia coli*, as a vaccine reported very high levels (about 95%) of protection[13]. The 45W antigen was used as a DNA vaccine in sheep and low levels of antibody, measured using a recombinant form of 45W, was observed[14].

Materials and Methods

Plasmids containing the CMV promoter and the genes encoding CTLA4, the Fc portion of human immunoglobulin (hIg) and the CD5 signal peptide were described above. The gene encoding 45W was obtained from Dr. Marshall Lightowlers (Dept. Veterinary Science, University of Melbourne).

Inbred Balb/c mice of 6-8 weeks of age were obtained from the Dept. Microbiology and Immunology Animal House, University of Melbourne.

Standard DNA manipulation and CsCl purification techniques were used. The gene encoding 45W was ligated into two DNA vaccines. Construct pCI::mCTLA4-hIg-45W expressed a fusion protein which comprised the CTLA4 signal peptide, mouse CTLA4 ectodomain, hIg and the 45W antigen. Construct pCI::CDSL-hIg-45W expressed a fusion protein which contained the signal peptide from CD5, hIg and the 45W antigen.

DNA (100 μg) was injected into the quadriceps of mice on days 0 and day 28. Sera was obtained at appropriate intervals post vaccination and analysed for total antibodies specific for recombinant 45W antigen in a titration ELISA[15] using horseradish peroxidase conjugated anti-mouse immunoglobulins.

Purified recombinant 45W(His)$_6$ was obtained from *E. coli* according to Rothel et al.[14] using a polyhistidine 'tag' and nickel affinity chromatography.

Results

Figure 10:
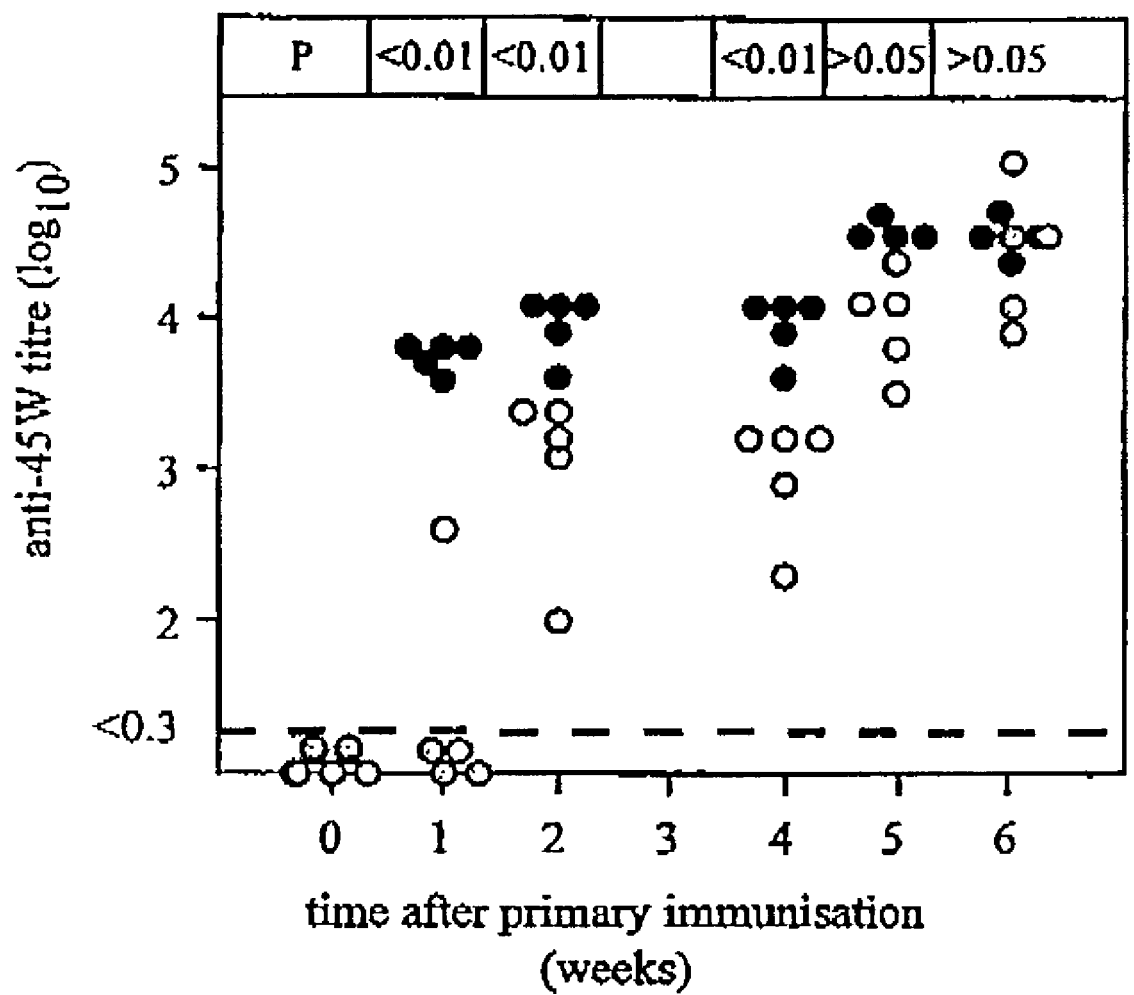

Mice were immunised with the DNA vaccines pCI::mCTLA4-hIg-45W, or pCI::CD5L-hIg-45W (FIG. 10). Mice received 100 ug of DNA on days 0 and 28 and were bled at weekly intervals. Mice receiving the DNA vaccine which expressed CTLA4 fused to the hIg/45W vaccine developed a more rapid antibody response than the mice which received a similar plasmid vaccine construct ie. pCI::CD5L-hIg-45W which did not contain the CTLA4 gene. The mice receiving the vaccine with CTLA4 produced serum antibodies of high titre (ie.≧10,000) on days 7, 14 and 28. In comparison, mice which received the construct lacking CTLA4 did not produce high titre antibodies (ie. titre≧10,000) until after the second immunisation on day 28. All mice(ie. 5/5) which received the DNA vaccine containing CTLA4 produced 45W-specific antibodies by 7 days post immunisation whereas only 1/5 animals which received the equivalent DNA vaccine lacking CTLA4 produced antibodies at day 7 post immunisation. The data was analysed using Student's t-test.

Figure 11:
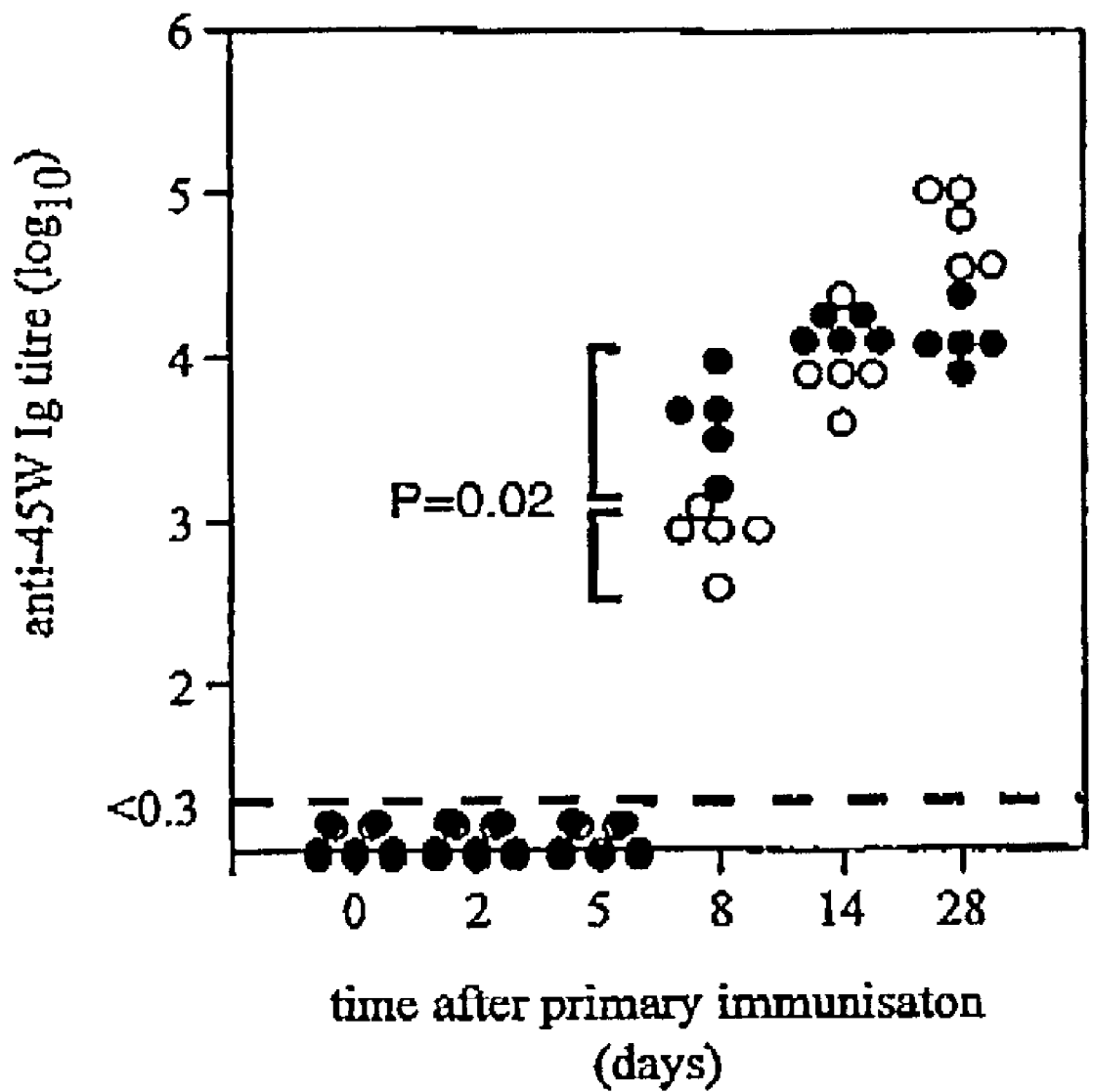

A second trial was undertaken where mice received either 20 μg of purified recombinant 45W(His)$_6$ protein in Complete Freund's Adjuvant, or the CTLA4 DNA vaccine (ie. pCI::mCTLA4-hIg-45)(FIG. 11). The serum antibody response was examined on days 0, 2, 5, 8, 14 and 28. The serum antibody response specific for 45W was higher at day 8 in DNA vaccinated mice than in mice which received the 45W protein vaccine.

Discussion

The murine serum antibody response to 45W DNA vaccination was accelerated by fusion of CTLA4 to the hIg-45W fusion protein. The antibody response to 45W correlates with protection in sheep against *T. ovis* disease. Addition of CTLA4 led to a more rapid high titre response, with a shorter unprotected period following immunisation. The effect of CTLA4 on the magnitude of the anti-45W response was not as dramatic as the effect on human Ig described above. This may have been due to the conformational restraints from the fusion of the various molecules or some inherent property of the 45W antigen. Furthermore, the immunisation protocol employed in this Example differed from Example 1 in that boosting occurred at 4 rather than two weeks. Due to the more rapid kinetics of the response via CTLA4 targeting boosting may not have been optimum and thus the magnitude was not effected.

EXAMPLE 4

Use of CTLA4 with AMA1 to Protect Against *Plasmodium chabaudi adami* in Mice

Introduction

AMA1[16] is a candidate vaccine antigen against malaria. We have evidence that domain3 of AMA1 folds independently and as such may be a good candidate in producing a fusion protein with hIg. However, although AMA1 has been shown to confer protection in mouse malaria[17], we are unaware of any work that has shown domain3 to be protective.

Materials and Methods

Plasmids containing the CMV promoter and the genes encoding CTLA4, the Fc portion of human immunoglobulin (hIg) and the CD5 signal peptide were described above. Domain 3 of AMA-1 from the *Plasmodium chabaudi adami* DS strain[16] was fused to CTLA4Ig and CD5LIg (pCI::mCTLA4-hIg-AMA and pCI::CD5L-hIg-AMA). The plasmid pCI::mCTLA4-hIg was used as a negative control.

Inbred female Balb/c mice of 6-8 weeks of age were used.

DNA (100 ug) was injected into the quadriceps of mice on day 0 only. Mice were challenged with *Plasmodium chabaudi adami* DS and the number of deaths recorded.

Antibody titres were measured by ELISA using refolded *E. coli* expressed entire ectodomain of AMA1[17]. The titres were expressed as the log of the reciprocal of the last serum dilution to give an OD>0.1.

Results

Figure 12:
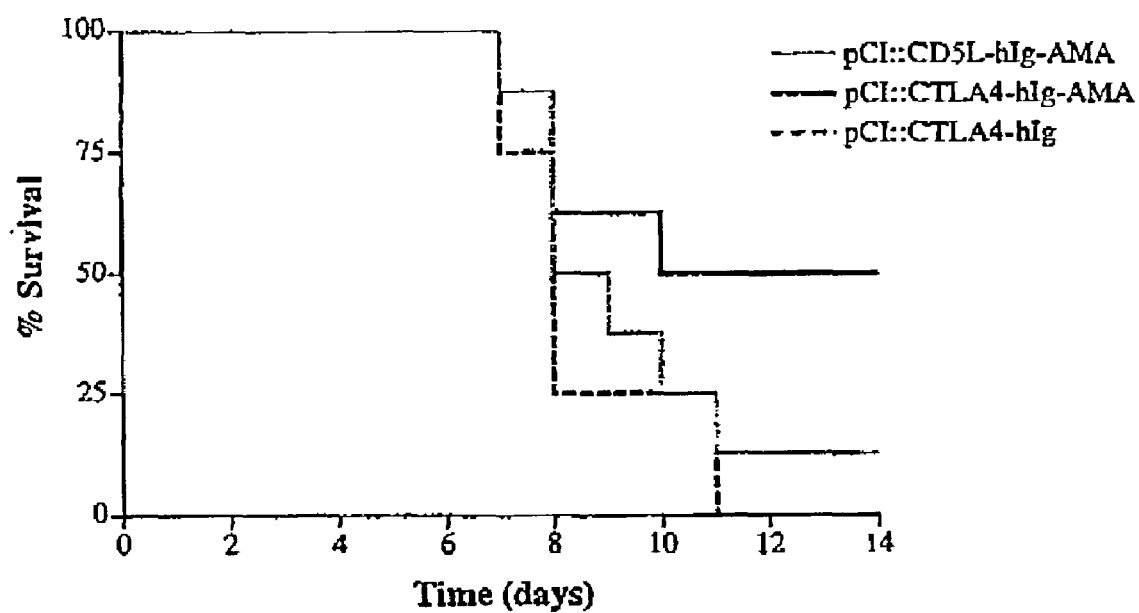
Figure 13:
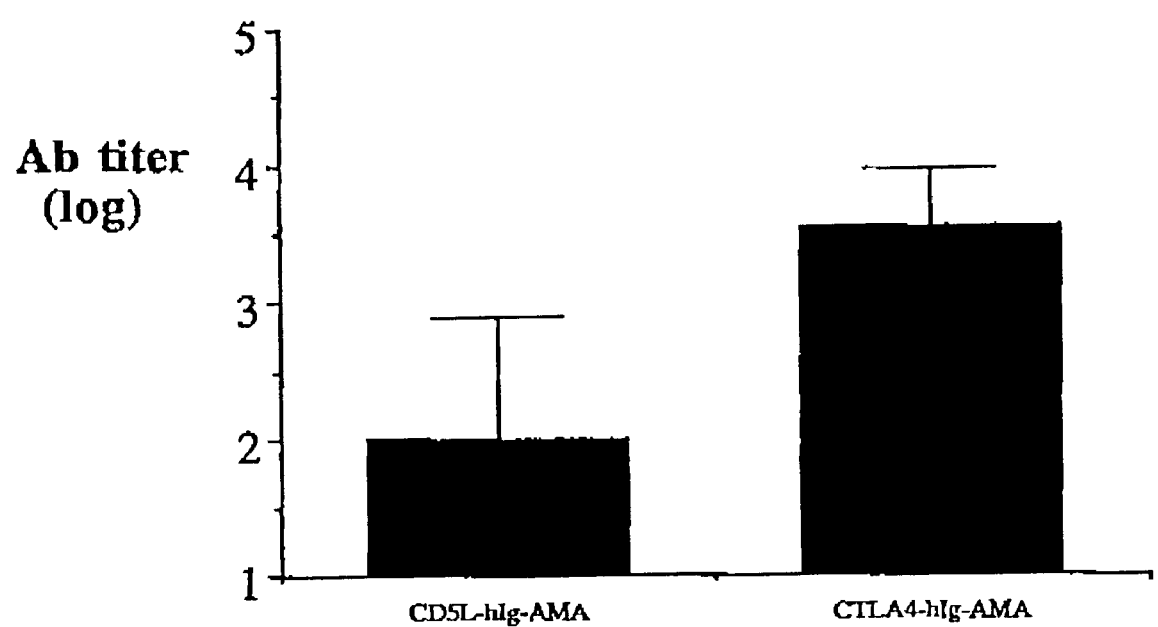
FIG. 13 shows antibody titres.
Figure 14:
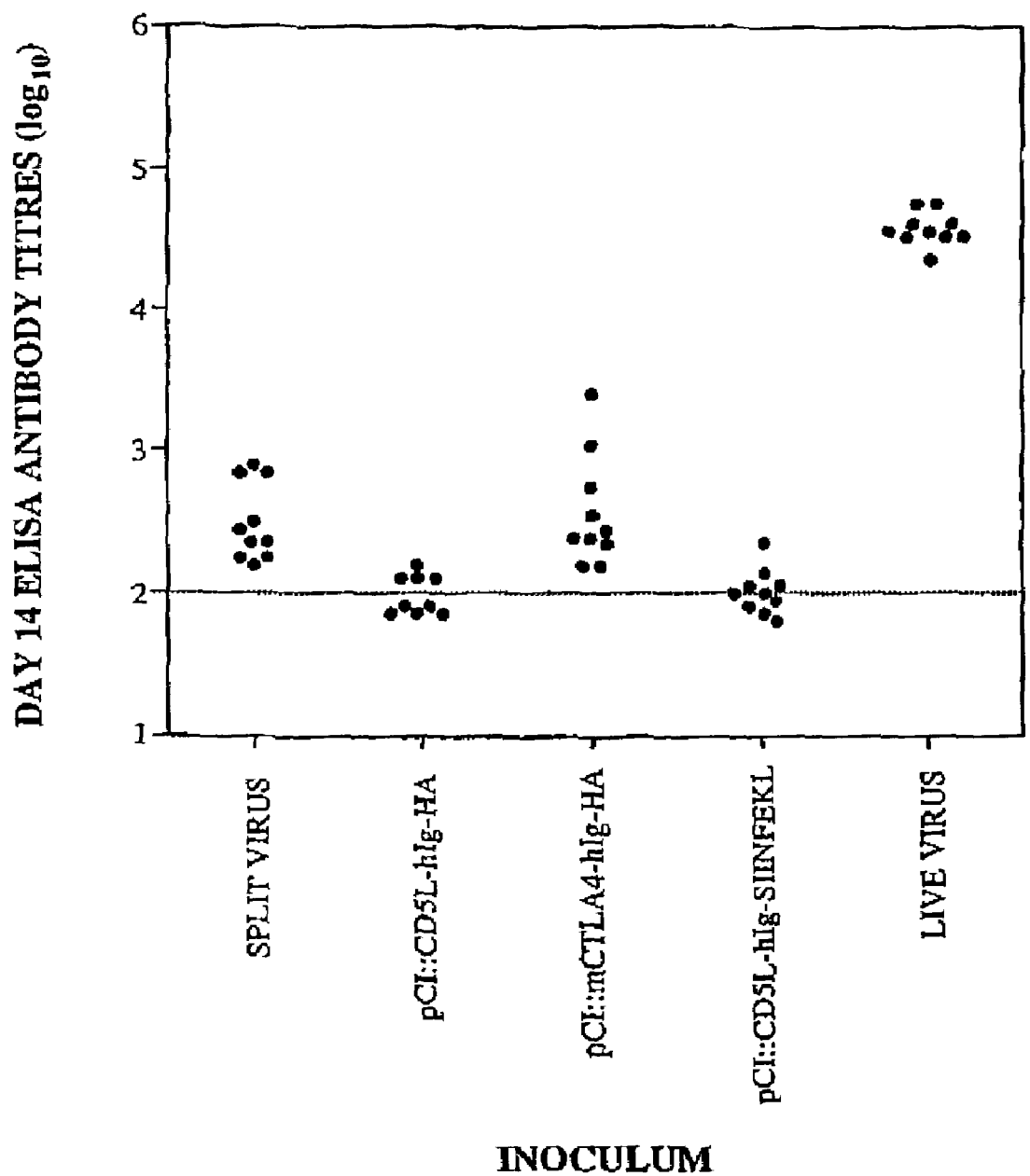
FIG. 14 shows antibody titres at day 14 with varying immunisations
Figure 15:
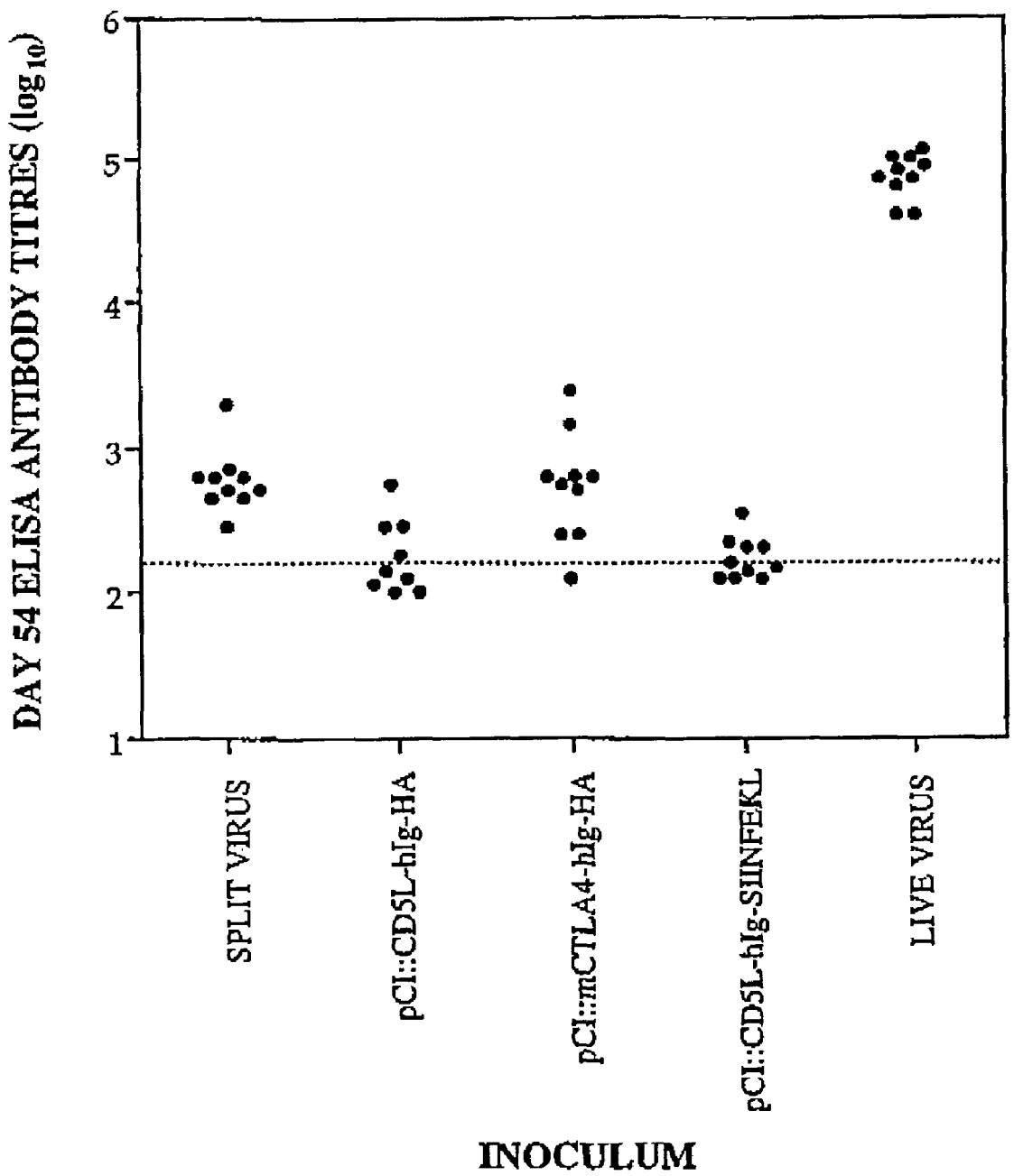
FIG. 15 shows antibody titres at day 54 with varying immunisations
Figure 16:
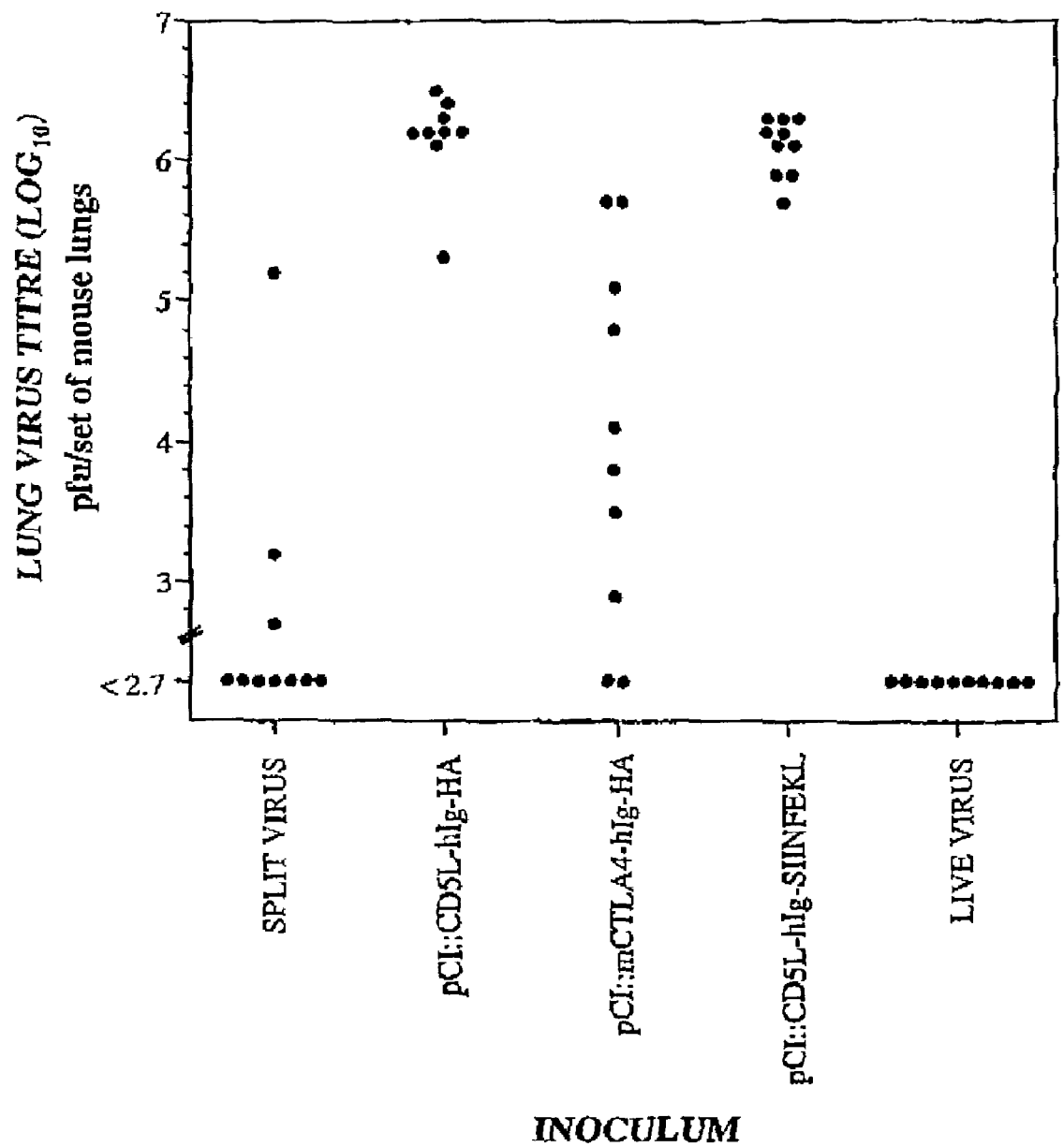
FIG. 16 shows lung virus titres

In the first trial, there were 8 mice per group. A single immunisation with the DNA vaccine pCI::mCTLA4-hIg-AMA afforded partial protection against an intraperitoneal challenge of 100,000 parasites (FIG. 12). Challenge was performed 14 days after immunisation. This was significant (log rank test; p<0.05) from the control pCI::mCTLA4-hIg group. There was a clear indication that the CTLA4 conferred better protection than the pCI::CD5L-hIg-AMA group, although this did not reach statistical significance. The antibody titres (FIG. 13) show that the CTLA4 targeting ligand enhances the antibody response to AMA1 (p<0.005).

A second trial was undertaken with larger group (16/group) and with an intravenous challenge of 10,000 parasites. No protection was seen in this second trial.

Discussion

In the first trial, CTLA4 conferred some protection against malaria by domain3 of antigen AMA1. This was not found in the second trial. We do not know why there was a difference between the two trials. Because there is not a full set of antibody data for comparison, we do not know whether the level of antibody achieved was sufficient in the mice that died in trial two, or whether the effect was due the different route of challenge. We also do not know how effective CTLA4IgAMA may be when booster doses are given.

EXAMPLE 5

Use of CTLA4 in Influenza Infection in Mice

Introduction

As an additional model for testing protective efficacy we have used influenza infection of the murine respiratory tract. The influenza haemagglutinin (HA) gene was cloned behind targeting molecules and the resulting DNA vaccines examined for their ability to generate higher anti-viral antibody titres and afford greater protection against live viral challenge compared to control vaccines not expressing the targeting molecule.

Materials and Methods

Virus

The type A influenza virus used in this study was PR8=A/Puerto Rico/8/34 (H1N1). Virus was grown in the allantoic cavity of 10-day embryonated hens' eggs for 2 days at 35° C. The allantoic fluid was collected and clarified by centrifugation (2000 g, 15 mins, 4° C.). Aliquots of allantoic fluid containing infectious virus were stored at −70° C. and used for immunisation and challenge of mice. Purified PR8 virus used in ELISA assays was obtained as zonally purified stocks from CSL Ltd, Parkville, Victoria, Australia. The haemagglutination assay[18] was used to quantitate virus and titres are expressed in haemagglutinating units (HAU) per ml.

Immunisation

Groups of 10 BALB/c mice were immunised intramuscularly (i.m.) under anaesthesia on day 0 with 0.1 ml of DNA vaccine containing 50 μg of plasmid. The constructs used for immunisation were pCI::CD5L-hIg-HA, pCI::mCTLA4-hIg-HA, which were based on PR8 HA lacking the signal and transmembrane sequences, and pCI::CD5L-hIg-SIINFEKL (expressing an 8 amino acid sequence from chicken ovalbumin) as a negative control. As a positive control, a group of 10 BALB/c mice were infected intranasally (i.n.) with 50 plaque forming units (pfu) of infectious PR8 virus and another group immunised subcutaneously with 1 μg of β-propiolactone (BPL)-inactivated and sodium taurodeoxycholate-disrupted PR8 virus (split virus). Serum samples were collected from all mice on days 7, 14 and 54 and mice were then challenged on day 65.

Intranasal Challenge of Mice and Preparation of Mouse Lung Extracts

Penthrane anaesthetised mice were challenged with 50 pfu of infectious PR8 influenza virus i.n. Each mouse received 50 μl of virus in the form of allantoic fluid diluted in phosphate buffered saline (PBS). Five days after challenge, mice were killed by cervical dislocation and lungs were removed and transferred aseptically to bottles containing 1.5 ml Hanks Balanced Salt Solution (HBSS), supplemented with 100 U of penicillin per ml, 100 μg of streptomycin per ml and 30 μg of gentamicin per ml. Lung homogenates were prepared using a tissue homogeniser. Each lung suspension was then centrifuged at 300×g for 5 minutes and the supernatants were removed, aliquoted and stored at −70° C. prior to assay for infectious virus.

Enzyme-linked Immunosorbent Assay

The enzyme-linked immunosorbent assay (ELISA) was performed as previously described by Jackson et al.[19] using 96-well polyvinyl microtitre trays (Dynatech, Australia) coated with a solution containing 50 HAU of purified PR8 virus per well. Antibody titres are expressed as the reciprocal of the antibody dilution giving an absorbance of 0.2 units.

Plaque Assay for Infectious Virus

Virus titres were determined by plaque assay on monolayers of Madin-Darby canine kidney (MDCK) cells in 35 mm petri dishes (Nunc, Roskilde, Denmark). The culture medium was RPMI-1640 supplemented with 2 mM glutamine, 2 mM sodium pyruvate, 100 U of penicillin per ml, 100 μg of streptomycin per ml, 30 μg of gentamicin per ml and 10% (vol/vol) foetal calf serum (heat inactivated at 56° C. for 30 min). Monolayers were washed with serum-free RPMI-1640 containing antibiotics and inoculated in duplicate with 100 μl of dilutions of lung homogenates in the same medium. After allowing 45 minutes in a humidified incubator (37° C., 5% $CO_2$) for virus adsorption, 3 ml of agarose overlay medium at 45° C. was added. Incubation was continued for a further 3 days and plaques counted. The agarose overlay medium was Leibovitz L-15 medium pH 6.8 (Gibco Laboratories, U.S.A.) supplemented with 100 U penicillin per ml, 100 μg of streptomycin per ml, 0.01 M HEPES buffer pH 6.8 (Calbiochem, Australia), 0.1% trypsin-TPCK (Worthington, Biological Systems Inc., U.S.A.) and 0.9% agarose (ICN Biomedicals Sydney, Australia).

Statistical Analysis

The data were analysed using the nonparametric Mann-Whitney U test which compares two sets of unpaired samples. The null hypothesis is that the two population medians are equal and the resultant P value for particular comparisons is given.

Results and Discussion

Serum Antibody Responses of Mice

Sera collected from mice immunised with the DNA constructs, split PR8 virus in PBS, or infectious PR8 virus were assayed for anti-viral antibody by ELISA. On day 7 after priming, only mice immunised with infectious PR8 virus exhibited anti-viral antibody titres significantly higher than the background titres detected in mice given the control DNA construct pCI::CD5L-hIg-SIINFEKL (p=0.0002). However by day 14, in addition to the high antiviral antibody titres detected in the virus infected mice, antibody titres of mice immunised with the pCI::mCTLA4-hIg-HA construct were significantly higher than those of mice given the control DNA constructs pCI::CD5L-hIg-HA (p=0.0003) or pCI::CD5L-hIg-SIINFEKL (p=0.0004) (FIG. 14). Furthermore, mice immunised with the pCI::mCTLA4-hIg-HA construct had comparable levels of antiviral antibody to mice given the split virus vaccine (p=0.97). The antiviral antibody titres of sera collected on day 54 post-priming were also determined (FIG. 15). Overall, the day 54 titres were similar to those measured in sera collected on day 14, and the level of antibody in the day 54 sera of mice given the pCI::mCTLA4-hIg-HA construct remained significantly higher than that of mice given pCI::CD5L-hIg-HA (p=0.009) or pCI::CD5L-hIg-SIINFEKL (p=0.0028), and comparable to split virus (p=0.85).

Ability of PR8 HA Constructs to Elicit Protective Immunity

Protection of vaccinated mice from influenza infection was assessed by examining the ability of mice to clear a challenge dose of virus from their lungs by five days post-infection. It should be noted that both antibody and cytotoxic T cell-mediated responses can lead to viral titre reduction within this 5 day interval. Mice were challenged on day 65 post-priming and the titre of virus in their lung was determined by a plaque assay. FIG. 16 shows that all mice immunised with infectious virus were able to clear the challenge dose of virus. Of the mice given DNA constructs, the lung virus titres of mice immunised with the pCI::mCTLA4-hIg-HA construct were significantly lower than those of mice immunised with either pCI::CD5L-hIg-HA (p=0.0004) or pCI::CD5L-hIg-SIINFEKL (p=0.0002). Also the level of clearance observed in the pCI::mCTLA4-hIg-HA construct-immunised mice was almost as good as that seen in mice given the split virus vaccine.

Conclusions pCI::CTLA4-hIg-HA conferred higher antibody levels and better protection against challenge compared with the control vector pCI::CDSL-hIg-HA demonstrating the immune enhancing effect of the incorporation of the targeting molecule.

EXAMPLE 6

Use of CTLA4 in *Corynebacterium pseudotuberculosis* in Sheep.

Introduction

*Corynebacterium pseudotuberculosis* is the causative agent of caseous lymphadenitis (CLA) in sheep. Established infection by these bacteria leads to the formation of abscesses in the lymph nodes, especially the draining lymph node of the site of infection. Phospholipase D (PLD) has been characterised as a virulence factor and a protective antigen for CLA. Indeed formalin-treated PLD[20] or genetically toxoided PLD (ΔPLD[22]) has been shown to protect sheep from CLA.

We have used the genetically toxoided PLD as the basis for our DNA vaccination approach and investigated whether the addition of bovine (b)CTLA4-hIg or hIg alone to the ΔPLD construct enhanced the immune response to PLD and to hIg.

Materials and Methods.

DNA Constructs

Using the known sequence of bCTLA4 (GenBank accession number X15070), the bCTLA4 gene was isolated from bovine peripheral blood mononuclear cells. A PCR product of bCTLA-4 (729 bp) was cloned into the Zeroblunt TM cloning vector according to the manufacturer's instructions (Invitrogen) and sequenced using the Applied Biosystems automated sequencer. The sequence of bCTLA4 was found to be identical to the published sequence.

The following constructs were generated in the pCI vector for DNA immunisation:

pCI::bCTLA4-hIg-ΔPLD pCI::ΔPLD pCI::bCTLA4-hIg pCI::CD5L-hIg-ΔPLD*

*CD5L refers to the leader sequence of the CD5 molecule allowing the huIg-ΔPLD protein to be secreted.

Experimental Animals and Immunisation Regimen

Cross-bred ewes aged 12 weeks were used in the challenge trial. 10 animals were allocated randomly to each group. Animals were pre-screened for the presence of antibodies to PLD and to *Corynebacterium pseudotuberculosis* lysate. Positive animals were excluded from the trial. Shearing, vaccination and tail docking of animals was avoided to minimise risk of infection with *Corynebacterium pseudotuberculosis*.

Animals were injected intra-muscularly with 500 µg LPS free pCI plasmid DNA (coding for either pCI::bCTLA4-hIg-ΔPLD, pCI::ΔPLD, pCI::bCTLA4-huIg or pCI::CD5L-huIg-ΔPLD) in 5 ml of PBS. Control animals received either Glan-vac or were left un-immunised. All animals received the same vaccine, at the same dose, 4 weeks later.

Challenge

Bacterial cultures of wild type *Corynebacterium pseudotuberculosis* were grown at 37° C. in Brain heart infusion broth (Difco Laboratories) containing 0.1% Tween 80 (BHI).

All sheep were challenged 6 weeks after primary immunisation using a 1 ml dose of $10^6$ CFU of *Corynebacterium pseudotuberculosis* injected just above the coronet of the right hind lateral claw.

Immunological Assays

Sera were collected from the sheep at weekly intervals and assayed for the presence of antibodies to genetically detoxified PLD (ΔPLD) and hIg using an ELISA. Plates were coated with 1/50 of culture supernatant from ΔPLD expressing *Corynebacterium pseudotuberculosis* or 5 g/ml hIg protein. The sera were diluted in two fold steps starting at 1/100 and 1/10 for the detection of anti-ΔPLD and anti-hIg antibodies respectively. Titres were calculated by linear regression on a double logarithmic scale in the linear part of the graph. The titre was defined as the dilution, which resulted in an O.D. 0.3 in the ELISA.

T cell proliferation assays were performed in triplicates using 2 concentrations of ΔPLD (1/50 and 1/250) or hIg (5 g/ml and 25 g/ml) as an antigen. PBMC were purified by ficoll gradient and cultured in vitro for 3 days. The cultures were pulsed with 3H-methyl-thymidine for 18 hours before being harvested on glass fibre filters and radioactive incorporation assessed. The results are presented as stimulation indices (i.e. ratio between counts obtained with antigen over counts obtained without antigen).

Statistical analysis was performed using the Systat program. The non-parametric Mann-Whitney U test was used to calculate significance. p values below 0.05 were considered significant.

Results

Anti-hIg Antibody Levels

The antibody titres to human immunoglobulin (hIg) reflect the immune response to the DNA vaccination against the hIg part of the fusion protein in the case of bCTLA4-hIg-ΔPLD, CD5L-hIg-ΔPLD and bCTLA4-hIg. By comparing the response to hIg from the animals injected with pCI::bCTLA4-hIg-ΔPLD to these injected with pCI::CD5L-hIg-ΔPLD it is possible to specifically evaluate the effect of bCTLA4 targeting on the immunogenicity of hIg. Results shown in FIG. 17 indicate that the antibody response to hIg in animals injected with pCI::bCTLA4-hIg-ΔPLD (filled squares) is both earlier and stronger than the anti-hIg response induced in animals immunised with pCI::CD5L-hIg-ΔPLD (closed circles). The Mann-Whitney U test indicates a statistically significant difference for weeks 3 and 4. Corroborating these results the anti-hIg response in the group injected with pCI::bCTLA4-hIg (closed triangles) is also earlier and stronger than the response in animals injected with pCI::CD5L-hIg-ΔPLD.

Anti-ΔPLD Antibody Levels

Immunisation with the detoxified-PLD protein antigen (Glan-Vac) resulted in little or no detectable antibodies during the first 7 weeks after immunisation. Two weeks after challenge antibody levels increased dramatically. This is consistent with previously reported results[21]

All groups immunised with pCI encoding the ΔPLD antigen either alone or as a fusion protein with bCTLA4-hIg or with CD5L-hIg, resulted in similar kinetics of antibody production. Indeed, no significant anti-ΔPLD antibody levels were detected until 2 weeks post-challenge (i.e. week 8). At each time point there was no significant difference between the level of antibodies induced by the different pCI constructs, indicating that all constructs have a similar ability to induce immune memory to ΔPLD. However, this result is not surprising in light of the fact that detoxified-PLD is not a classical antigen in that two doses of the protein antigen (Glan-Vac group) failed to induce substantial antibody levels. This result has also been reported by others[22]. Thus detoxified-PLD seems to result in the induction of immune memory without induction of high antibody titres. This immune memory is then activated during the early stage of the challenge by PLD expressed by *Corynebacterium pseudotuberculosis*. It is interesting to note that ΔPLD expressed in eukaryotic cells (COSm6 cells) has a slightly larger size compared to ΔPLD expressed in *Corynebacterium pseudotuberculosis* (FIG. 18). This difference can be accounted for by the possible glycosylation of ΔPLD in eukaryotic cells. As in the case with anti-hIg antibody levels it is noted that sheep, in contrast to mice, do not produce antibodies over prolonged periods of time following DNA vaccination.

T Cell Responses to ΔPLD and hIg.

T cell responses to ΔPLD and hIg were analysed at 3 weeks, 6 weeks and 9 weeks. No significant antigen specific proliferation, to these two antigens could be demonstrated in peripheral blood mononuclear cells (PBMC) at any time point. This is most likely due to technical difficulties since the kinetics of the anti ΔPLD response indicate the likely presence of memory T cells in the vaccinated animals.

Anti-ΔPLD Response Subsequent to Challenge with Virulent *C. pseudotuberculosis*.

Challenge was performed at 6 weeks post-immunisation (i.e. two weeks post-booster immunisation). Observation of the site of inoculation at week 10 did not reveal any correlation with immunisation regime. Except in the case of the unvaccinated control and pCI::bCTLA4-hIg immunised animals, the antibody response to ΔPLD increased two weeks post-challenge (week 8). This indicates that the immune memory induced by the immunisation with DNA can be boosted with ΔPLD produced by *Corynebacterium pseudotuberculosis*. This indicates that although ΔPLD produced by DNA vaccination is most likely glycosylated there is still cross-reaction with bacterial wild-type PLD.

In the un-immunised control animals the level of anti-ΔPLD antibodies remains low until 3 to 4 weeks post-challenge (week 9). This kinetics of antibody appearance has been described previously[22].

Interestingly the antibody levels in the animals primed with ΔPLD by DNA vaccination or detoxified-PLD by Glan-Vac injection, diminished after week 8 suggesting that the PLD antigen is no longer boosting the immune response. This may be due to a diminished level of PLD secretion due to the animals clearing *Corynebacterium pseudotuberculosis*.

Protection from Challenge with Virulent *Corynebacterium pseudotuberculosis*.

At week 12 post vaccination (6 weeks post challenge) necropsy of all animals was performed to evaluate the protective efficacy of the immunisation protocol. Both left and right popliteal, inguinal and prefemoral lymph nodes were dissected and visually assessed for the characteristic abscesses induced by *Corynebacterium pseudotuberculosis*. The lungs were palpated to detect abscesses and no lung abscesses were found in any of the animals. Protection was defined as the absence of the characteristic *Corynebacterium pseudotuberculosis* abscesses in any of the lymph nodes. In two sheep small dry lesions were observed in the draining popliteal lymph node, clearly distinct from the abscesses in the other animals. These lesions were most likely foci of *Corynebacterium pseudotuberculosis* which were regressing in the face of an effective immune response and these animals were also scored as "protected". From FIG. 19 it can be seen that while about 10% of the unvaccinated animals did not develop lesions, 90% were protected by vaccination with Glan-Vac. Only 1 animal out of 10 injected with pCI::CTLA4-hIg did not have abscesses in the lymph nodes. All animals vaccinated with DNA encoding for ΔPLD (pCI::bCTLA4-hIg-ΔPLD, pCI::ΔPLD and pCI::CD5L-hIg-ΔPLD) were afforded some protection. The level of protection ranged from 40 to 70% with the highest degree of protection observed in the group injected with pCI::CTLA4-hIg-ΔPLD.

Conclusion

This study has examined the ability of bCTLA4 to increase the immune response to antigens during DNA immunisation in sheep. bCTLA4 has the ability to accelerate and increase the immune response to hIg. Challenge with *Corynebacterium pseudotuberculosis* indicated that DNA vaccination could induce a protective immune response. When comparing the protection obtained with pCI::bCTLA4-hIg-ΔPLD and pCI::CD5L-hIg-ΔPLD a substantial difference was observed.

The protection induced by CD5L-hIg-ΔPLD is lower than the protection induced by ΔPLD on its own. This difference may be due to the fact that the ΔPLD molecule is much smaller than the bCD5L-hIg-ΔPLD and hence could be expressed in an acceptable conformation more easily. One could therefore expect that the bCTLA4-hIg-ΔPLD molecule which is even larger would be even more difficult to express. Hence the fact that the bCTLA4-hIg-ΔPLD molecule induced higher levels of protection indicates that the CTLA4 molecule effectively increases the immunogenicity of the fusion protein. It can be reasonably expected that by improving the level of expression and folding of the molecule even better protection could be obtained. One way of achieving this would be to reduce the size of the hIg portion of the fusion protein.

EXAMPLE 7

Vaccination of C3H/He Mice with DNA Encoding the Parasite Surface Antigen 2 (PSA2) of *Leishmania major*.

Introduction

Protection against infection with this obligatory intracellular parasite is provided by CD4+ T cells of the macrophage activating, Th1 type. We have shown that injection of plasmid DNA encoding full length PSA2 induced significant protection against a challenge infection in C3H/He mice. This protection correlated with the induction of a very low, but consistent Th1 type of immune response, ie induction of T cells secreting interferon gamma, but no IL-4. Here we aim to examine the ability of CTLA4-Ig to improve the level of protection.

Materials and Methods

PSA2 encoding residues 33-357 (missing the leader and gpi signal) was fused C-terminal to either pCI::CD5L-hIg or pCI::mCTLA4-hIg. DNA encoding a secreted form of PSA2 (residues 1-357) was also made (pCI::PSA2) Groups of 8 mice were injected with 100 μg DNA in 100 μl phosphate buffered saline (PBS) intramuscularly twice at two week intervals. Two weeks after each injection the mice were bled and the serum tested for antibodies to PSA-2. Two weeks after the second injection the mice were infected intradermally with 100,000 promastigotes. The development of lesions at the site of infection was monitored weekly and scored according to size. Parasite burdens in the lymph nodes draining the lesion were determined by limiting dilution analysis at 7 weeks after challenge infection.

Results

Antibody Production

Antibodies were measured only by ELISA OD at a single point. Two weeks after the first immunisation, 4 of 8 mice immunised with pCI::mCTLA4-hIg-PSA2 and 3 of 8 mice given pCI::CD5L-hIg-PSA2 produced significant antibody at a dilution of 1:500. However, after the second injection of DNA mice immunised with pCI::mCTLA4-hIg-PSA2, pCI::CD5L-hIg-PSA2 and our own secreted form of PSA-2 showed significant levels of antibody at this dilution. The PBS control had background antibody.

Protection from Infection

Mice immunised with DNA encoding pCI::CD5L-hIg-PSA2 and the controls PBS and vector DNA developed lesions at the site of infection 1 week after challenge. Mice immunised with pCI::mCTLA4-hIg-PSA2 or pCI::PSA2 developed lesions only 3 weeks after infection and the size of the lesions was smaller compared to the rest. Mice immunised with pCI::mCTLA4-hIg-PSA2 or pCI::PSA2 also had the smallest number of mice which developed lesions with only 5 of 8 mice showing any lesions at the peak of the disease curve (FIG. 20). Notably, pCI::mCTLA4-hIg-PSA2 conferred better protection than pCI::CD5L-hIg-PSA2 (p=0.0001; log rank test).

Summary

The ability to overcome the problem of low or absent responsiveness in DNA immunisation by antigen targeting enhances the potential of genetic vaccines. The present inventors also show that intramuscular injection of DNA can also be employed to deviate immune responses to the same antigen allowing for the development of vaccines in which the response most likely to confer protection can be generated.

Intramuscular injection of expression plasmids shows great potential for genetic vaccination. The present inventors have shown that fusion proteins consisting of antigen and cell surface receptor ligands could deliver antigen to sites of immune induction which enhance the immune response and possibly the efficacy of genetic vaccines. As set out above mice were immunized with plasmids encoding Fc fragment of human IgG1 as antigen. This Ig fragment was fused with CTLA4 (CTLA4Ig) for delivery to antigen presenting cells (APC) expressing B-7, or with L-selectin (L-SELIg) for delivery to high endothelial venule cells of lymph nodes. L-selectin binds CD34 and MadCAM-1 and so could target any lymphoid organ with these receptors (12). Enhanced antibody responses were shown in both the CTLA4Ig and L-SELIg immunized mice, 1000 and 100 fold respectively at 4 weeks. Moreover the response after CTLA4Ig immunisation was the most rapid. Immune deviation from an IgG2a to an IgG1 dominated response occurred in CTLA4Ig immunized mice and allows for the development of genetic vaccines in which the response most likely to confer protection can be generated.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Ulmer, J. B., J. J. Donnelly, S. E. Parker, G. H. Rhodes, P. L. Feigner, V. J. Dwarki, S. H. Gromkowski, R. R. Deck, C. M. De Witt, A. Friedman, L. A. Hawe, K. R. Laender, D. Martinez, H. C. Perry, J. W. Shiver, D. L. Montgomery, and M. A. Liu. 1993. Heterologous protection against influenza by injection of DNA encoding a viral protein. *Science* 259:1745.
2. Wolff, J. A., P. Williams, G. Acsadi, S. Jiao, A. Jani, and W. Chong. 1991. Conditions affecting direct gene transfer into rodent muscle in vivo. *Biotechniques* 11:474.
3. Hohlfeld, R., and A. G. Engel. 1994. The immunobiology of muscle. *Immunol. Today* 15:269.
4. Pardoll, D. M., and A. M. Beckerleg. 1995. Exposing the immunology of naked DNA vaccines. *Immunity* 3:165.
5. Raz, E., D. A. Carson, S. E. Parker, T. B. Parr, A. M. Abai, G. Aichinger, S. H. Gromkowski, M. Singh, D. Lew, M. A. Yankauckas, S. M. Baird and G. H. Rhodes. 1994. Intradermal gene immunization: the possible role of DNA uptake in the induction of cellular immunity to viruses. *Proc. Natl. Acad. Sci.* 91:9519.
6. Condon, C., S. C. Watkins, C. M. Celluzzi, K. Thompson and L. D. Falo, Jr. 1996. DNA-based immunization by in vivo transfection of dendritic cells. *Nature Med.* 2:1122.
7. In *Molecular cloning: A laboratory manual.* 2nd ed. 1989. J. Sambrook, E. F. Fritsch, and T. Maniatis, eds. Cold Spring Harbor Press, Cold Spring Harbor, N.Y., p1.38.
8. Aida, Y., and M. J. Pabst. 1990. Removal of endotoxin from protein solutions by phase separation using Triton X-114. *J. Immunol. Methods.* 132:191.
9. Major M. E., L. Vitvitski, M. A. Mink, M. Schleef, R. G. Whalen, C. Trepo and G. Inchauspe. 1995. DNA-based immunization with chimeric vectors for the induction of immune responses against the hepatitis C virus nucleocapsid. *J. Virol* 69:5798.
10. Manickan, E., R. J. Rouse, Z. Yu, W. S. Wire, and B. T. Rouse. 1995. Genetic immunization against herpes simplex virus. Protection is mediated by CD4 + T lymphocytes. *J. Immunol.* 155:259.
11. Linsley P. S., P. M. Wallace, J. Johnson, M. G. Gibson, J. L. Greene, J. A. Ledbetter, C. Singh and M. A. Tepper. 1992. Immunosuppression in vive by a soluble form of the CTLA-4 T cell activation molecule. *Science* 257:792.
12. Varki A. 1994. Selectin Ligands. *PNAS* 91:7390.
13. Rickard M D (1991). Cestode vaccines. Southeast Asian J Trop Med Public Health 22 Suppl:287-290.
14. Rothel J S, Waterkeyn J G, Strugnell R A, Wood P R, Seow H F, Vadolas J, Lightowlers M W. (1997) Nucleic acid vaccination of sheep: Use in combination with a conventional adjuvanted vaccine against *Taenia ovis*. Immunol Cell Biol 75:41-46.
15. Rothel J S, Lightowlers M W, Seow H F, Wood P R, Rothel L J, Heath D D, Harrison G B. (1996) Immune responses associated with protection in sheep vaccinated with a recombinant antigen from *Taenia ovis*. Parasite Immunol 18:201-208.
16. Hodder A N, Crewther P E, Matthew M L, Reid G E, Moritz R L, Simpson R J, Anders R F (1996) The disulfide bond structure of Plasmodium apical membrane antigen-1. J Biol Chem 271:29446-52.
17. Crewther P E, Matthew M L, Flegg R H, Anders R F (1996) Protective immune responses to apical membrane antigen 1 of *Plasmodium chabaudi* involve recognition of strain-specific epitopes. Infection & Immunity. 64:3310-7
18. Fazekas de St. Groth, Webster R G (1966) Disquisitions of Original Antigenic Sin. I. Evidence in man. J Exp Med 124:331-45
19. Jackson D C, Tang X L, Brown L E, Murray J M, White D O, Tregear G W (1986) Antigenic determinants of influenza virus hemagglutinin. XII. the epitopes of a synthetic peptide representing the C-terminus of HA1. *Virology* 155: 625-32
20. Burrell D H (1983) Caseous lymphadenitis vaccine NSW Vet. Proc. 19, 53-57
21. Hodgson A L, Krywult J, Corner L A, Rothel J S, Radford A J (1992) Rational attenuation of *Corynebacterium pseudotuberculosis*: potential cheesy gland vaccine and live delivery vehicle. Infect Immun 60, 2900-2905
22. Hodgson A L, Tachedjian M, Corner L A, Radford A J (1994) Protection of sheep against caseous lymphadenitis by use of a single oral dose of live recombinant *Corynebacterium pseudotuberculosis*. Infect Immun 62, 5275-5280

The invention claimed is:

1. A method of raising an immune response against an antigen or epitope of a pathogen in an animal comprising administering to said animal an amount of a DNA molecule sufficient to elicit or enhance a protective immune response against said pathogen, wherein said DNA molecule comprises: (i) a nucleotide sequence encoding CTLA4; (ii) a nucleotide sequence encoding said antigen or epitope; and optionally (iii) a nucleotide sequence encoding a polypeptide that promotes dimerization or multimerization of the product encoded by the DNA molecule.

2. The method of claim 1, wherein the DNA molecule comprises a nucleotide sequence encoding a polypeptide that promotes dimerization or multimerization of the product encoded by the DNA molecule.

3. The method of claim 1, wherein the CTLA4 targets a lymphoid cell, lymphoid site or an antigen presenting cell (APC).

4. The method of claim 1, wherein the immune response comprises the production of antibodies against the antigen or epitope.

5. The method of claim 4, wherein antibody production comprises immunoglobulin G1 (IgG1) production.

6. The method of claim 1, wherein the DNA molecule is contained within a vector.

7. The method of claim 1, wherein the DNA molecule is administered in a composition comprising said DNA molecule and a pharmaceutically acceptable carrier, diluent or excipient.

* * * * *

UNITED STATES PATENT AND TRADEMARK OFFICE
CERTIFICATE OF CORRECTION

| | | |
|---|---|---|
| PATENT NO. | : 7,423,023 B2 | Page 1 of 1 |
| APPLICATION NO. | : 10/185799 | |
| DATED | : September 9, 2008 | |
| INVENTOR(S) | : Boyle et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 726 days.

Signed and Sealed this

Eighth Day of February, 2011

David J. Kappos
*Director of the United States Patent and Trademark Office*